(12) United States Patent
Jin

(10) Patent No.: US 9,640,767 B1
(45) Date of Patent: May 2, 2017

(54) ELECTRONIC DEVICE INCLUDING PHOSPHINE OXIDE FUNCTIONALIZED TRIAZINE DERIVATIVE AND NOVEL PHOSPHINE OXIDE FUNCTIONALIZED TRIAZINE DERIVATIVE

(71) Applicant: PUSAN NATIONAL UNIVERSITY INDUSTRY-UNIVERSITY COOPERATION FOUNDATION, Busan (KR)

(72) Inventor: Sung Ho Jin, Busan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 15/169,119

(22) Filed: May 31, 2016

(30) Foreign Application Priority Data

Nov. 18, 2015 (KR) ......... 10-2015-0161609

(51) Int. Cl.
| | | |
|---|---|---|
| C07D 251/30 | (2006.01) | |
| C07F 9/6521 | (2006.01) | |
| H01L 51/00 | (2006.01) | |
| H01L 51/42 | (2006.01) | |
| H01L 51/10 | (2006.01) | |

(52) U.S. Cl.
CPC ........ H01L 51/0067 (2013.01); C07D 251/30 (2013.01); C07F 9/65212 (2013.01); *H01L 51/0036* (2013.01); *H01L 51/0037* (2013.01); *H01L 51/0043* (2013.01); *H01L 51/0047* (2013.01); *H01L 51/10* (2013.01); *H01L 51/424* (2013.01); *H01L 51/4253* (2013.01)

(58) Field of Classification Search
CPC .... C07D 251/30; C09K 11/06; H01L 51/5032
USPC ..................... 544/214; 345/82, 76
See application file for complete search history.

(56) References Cited

U.S. PATENT DOCUMENTS

2016/0013427 A1\* 1/2016 Kim ................... H01L 51/0074
257/40

FOREIGN PATENT DOCUMENTS

KR 10-2014-0112494 8/2014

OTHER PUBLICATIONS

Azimi, et al., A Universal Interface Layer Based on an Amine-Functionalized Fullerene Derivative with Dual Functionality for Efficient Solution Processed Organic and Perovskite Solar Cells, Adv. Energy Mater. 2015, 5, 1401692.
Bulliard, et al. Enhanced Performance in Polymer Solar Cells by Surface Energy Control, Adv. Funct. Mater. 2010, 20, 4381-4387.
Lin, et al., Enhanced Charge Separation by Sieve-Layer Mediation in High-efficiency Inorganic-Organic Solar Cells, Adv. Mater. 2009, 21, 759-763.
Stubhan, et al. Increasing the Fill Factor of Inverted P3HT:PCBM Solar Cell Through Surface Modification of Al-Doped ZnO via Phosphonic Acid-Anchored C60 SAMs, Adv. Energy Mater. 2012, 2, 532-535.

\* cited by examiner

*Primary Examiner* — Venkataraman Balasubramanian
(74) *Attorney, Agent, or Firm* — Knobbe Martens Olson & Bear, LLP

(57) ABSTRACT

Provided are an electronic device including a novel structured interface material capable of improving interface properties of the electronic device, and the novel interface material, and more specifically, an electronic device including the interface material of the present disclosure to allow easy extraction and injection of electrons, thereby exhibiting excellent interface properties, and a phosphine oxide functionalized triazine derivative having a structure in which an electron acceptor phosphine oxide group is substituted in 1,3,5-triazine-based skeleton, which is the interface material.

7 Claims, 9 Drawing Sheets

ELECTRONIC DEVICE INCLUDING PHOSPHINE OXIDE FUNCTIONALIZED TRIAZINE DERIVATIVE AND NOVEL PHOSPHINE OXIDE FUNCTIONALIZED TRIAZINE DERIVATIVE

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of Korean Patent Application No. 10-2015-0161609, filed on Nov. 18, 2015. The aforementioned application is incorporated by reference herein in its entirety, and is hereby expressly made a part of this specification.

TECHNICAL FIELD

The following disclosure relates to an electronic device using a novel phosphine oxide functionalized triazine derivative, and the novel phosphine oxide functionalized triazine derivative.

BACKGROUND

A solar cell technology is to directly convert light, that is, solar energy into electric energy by utilizing a photovoltaic effect, and most commercialized solar cells are inorganic solar cells using inorganic materials such as silicon, etc. However, the inorganic solar cells have disadvantages in that manufacturing cost is increased due to a complicated manufacturing process, and high-priced materials are required, and accordingly, research into a dye-sensitized solar cell and an organic solar cell manufactured with low cost through a relatively simple manufacturing process and with low-priced materials has been actively conducted.

The organic solar cell has been expected to be a low-priced solar cell in the future since it is capable of being manufactured with simple manufacturing processes and low installation expenses as compared to conventional silicon or compound semiconductor solar cells. A number of materials, structures, etc., of the organic solar cell have currently researched to improve efficiency of solar cells. Among them, a bulk heterojunction structure using mixture of electron donors and electron acceptors is known to have the highest efficiency.

However, in the bulk heterojunction structure, a diffusion distance of excitons which are electron-hole pairs formed by electron donors such as conductive polymers, etc., by sun light is only about 10 nm in the polymer. Accordingly, when the excitons do not reach interfaces of the electron donors and the electron acceptors within this distance, they reunite again and become extinct. In addition, after the excitons are separated into electrons and holes at the interfaces of the electron donors and the electron acceptors, the respective electrons and holes move toward a metal electrode and a transparent electrode, respectively. To this end, it is required that all of the electron donors are linked to be in contact with an anode, and all of the electron acceptors are linked to be in contact with a cathode while having a co-continuous structure. However, the structures of the electron donors and the electron acceptors may not be artificially determined, but depend on phase separation properties after mixing materials, and accordingly, it is not possible to obtain the ideal structure.

To obtain facilitate electron injection in the modern optoelectronic devices such as the organic solar cell, the incorporation of solution processed interfacial layers on stable metal electrodes has been widely used. The appropriate choice of interface materials administer a platform to carefully regulate the electrode work function (WF), protect the semiconductor layer from the diffusion of electrodes, mitigate the charge accumulation and recombination at the electrodes.

In order to improve the interface properties, CsF, LiF, $Cs_2CO_3$, conjugated or non-conjugated polymer electrolytes, fullerene derivatives, etc., are used. However, this method has problems in that an effect for improving interface properties is not significant, reactivity with air and water is high, synthesis and purification methods are complicated, reproducibility in batches is low, and only a deposition via expensive vacuum deposition is applicable, and further, it is difficult to apply a solution process in manufacturing a large area device.

Documents related to solar cell technology include Korean Patent Laid-Open Publication No. 10-2014-0112494; *Adv. Funct. Mater.* 20, 4381-4387 (2010); *Adv. Energy Mater.* 2, 532-535 (2012); *Adv. Mater.* 21, 759-763 (2009); and *Adv. Energy Mater.* 5, 1401692 (2015).

SUMMARY

An embodiment of the present disclosure is directed to providing an electronic device including a novel phosphine oxide functionalized triazine derivative.

Accordingly, in a generally applicable first aspect (i.e., independently combinable with any of the aspects or embodiments identified herein), there is provided an electronic device including a phosphine oxide functionalized triazine derivative represented by Chemical Formula 1 below as an interface material:

[Chemical Formula 1]

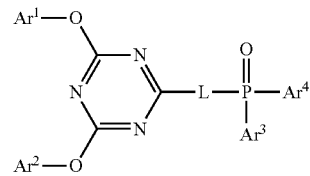

in Chemical Formula 1, $Ar^1$ and $Ar^2$ are each independently selected from (C6-C20)aryl unsubstituted and (C6-C20)aryl substituted with fluorine; L is (C6-C20)arylene substituted with at least one fluorine; $Ar^3$ and $Ar^4$ are each independently selected from (C1-C20)alkyl, (C6-C20)aryl, and (C3-C20)heteroaryl, wherein the alkyl, aryl, or heteroaryl of $Ar^3$ and $Ar^4$ are optionally substituted with one or more moieties selected from (C1-C20)alkyl, halo(C1-C20)alkyl, (C1-C20)alkoxy, and halo(C1-C20)alkoxy; and wherein the heteroaryl includes at least one heteroatom selected from N, O, and S.

In an embodiment of the first aspect (i.e., independently combinable with any of the aspects or embodiments identified herein), the electronic device can be selected from an organic solar cell, a perovskite solar cell, an organic field-effect transistor, and an organic thin film transistor.

In an embodiment of the first aspect (i.e., independently combinable with any of the aspects or embodiments identified herein), L can be (C6-C20)arylene substituted with at least two fluorines.

In an embodiment of the first aspect (i.e., independently combinable with any of the aspects or embodiments identified herein), $Ar^1$ and $Ar^2$ can each be independently selected from phenyl, biphenyl, naphthyl, anthryl, phenanthryl, tetracenyl, pyrenyl, and perylenyl, wherein the phenyl, biphenyl, naphthyl, anthryl, phenanthryl, tetracenyl, pyrenyl, or perylenyl of $Ar^1$ and $Ar^2$ can be optionally substituted with one or more fluorines; $Ar^3$ and $Ar^4$ can each be independently selected from methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, and pyrazinyl, and wherein the methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, or pyrazinyl of $Ar^3$ and $Ar^4$ can be optionally substituted with one or more moieties selected from methyl, ethyl, propyl, butyl, trifluoromethyl, perfluoroethyl, methoxy, trifluoromethoxy, and perfluoroethoxy.

In an embodiment of the first aspect (i.e., independently combinable with any of the aspects or embodiments identified herein), L can be selected from phenylene, biphenylene, naphthylene, anthrylene, phenanthrylene, tetracenylene, pyrenylene, and perylenylene, wherein L can be substituted with at least two fluorines.

In an embodiment of the first aspect (i.e., independently combinable with any of the aspects or embodiments identified herein), the phosphine oxide functionalized triazine derivative can be represented by Chemical Formula 2, Chemical Formula 3, or Chemical Formula 4:

[Chemical Formula 2]

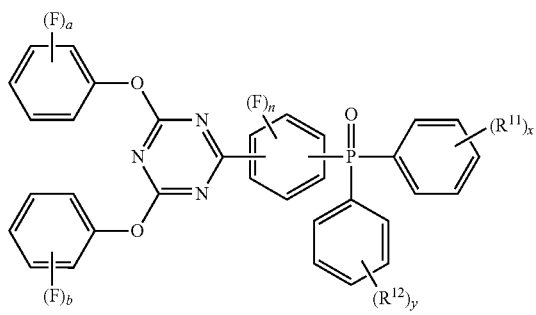

[Chemical Formula 3]

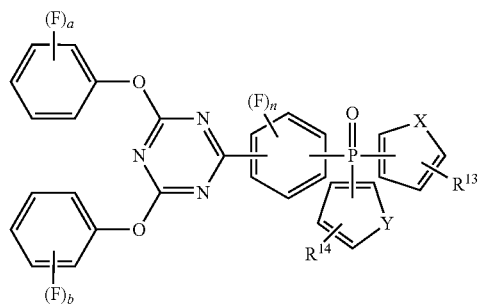

[Chemical Formula 4]

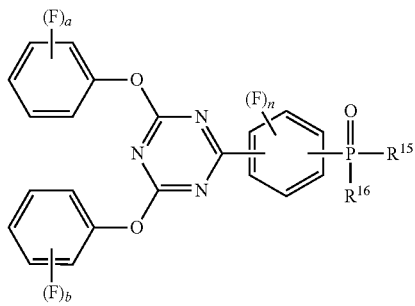

wherein a and b can each independently be an integer from 0 to 5; n can be an integer from 2 to 4; $R^{11}$ and $R^{12}$ can each independently be (C1-C20)alkyl, halo(C1-C20)alkyl, (C1-C20)alkoxy, or halo(C1-C20)alkoxy; x and y can each independently be an integer from 0 to 5; X and Y can each independently be selected from NH, O, and S; $R^{13}$ and $R^{14}$ can each independently be selected from hydrogen, (C1-C20)alkyl, halo(C1-C20)alkyl, (C1-C20)alkoxy, and halo(C1-C20)alkoxy; $R^{15}$ and $R^{16}$ can each independently be (C1-C20)alkyl, wherein the alkyl of $R^{15}$ and $R^{16}$ can be optionally substituted with one or more moieties selected from (C1-C20)alkyl, halo(C1-C20)alkyl, (C1-C20)alkoxy, and halo(C1-C20)alkoxy.

In an embodiment of the first aspect (i.e., independently combinable with any of the aspects or embodiments identified herein), the phosphine oxide functionalized triazine derivative may be selected from the following compounds, but the present disclosure is not limited thereto:

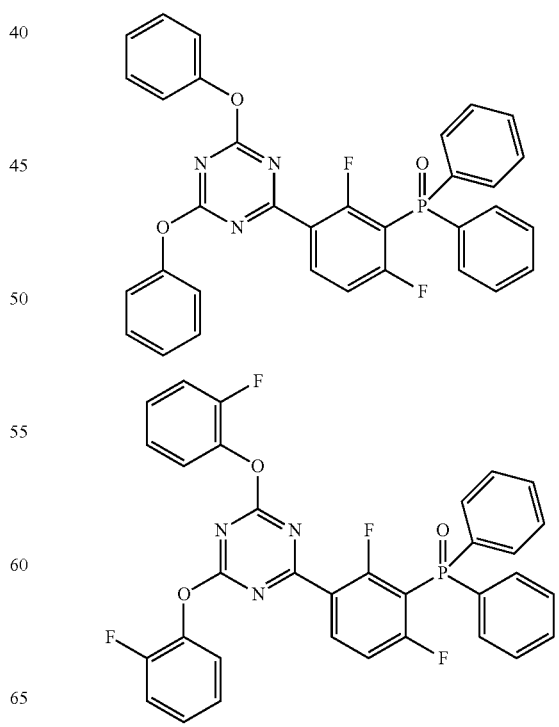

-continued
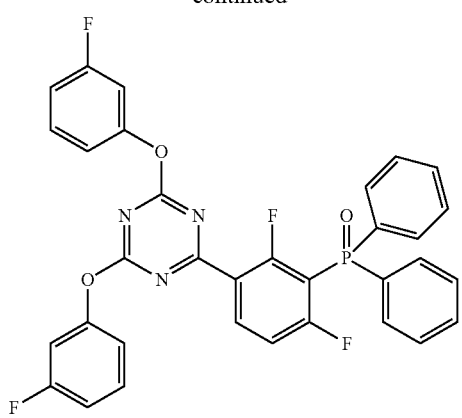
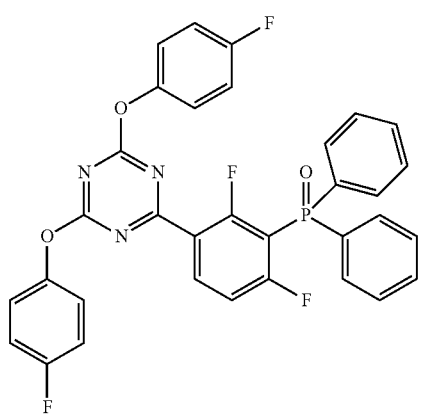
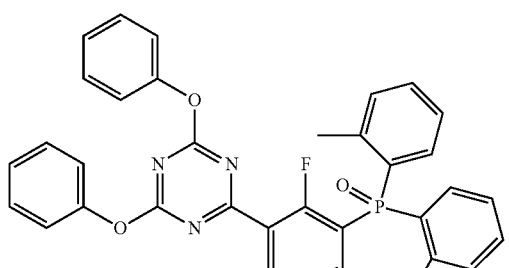
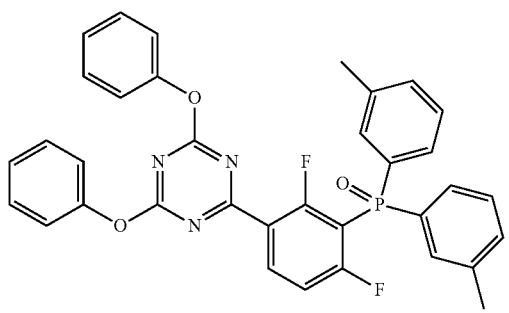
-continued
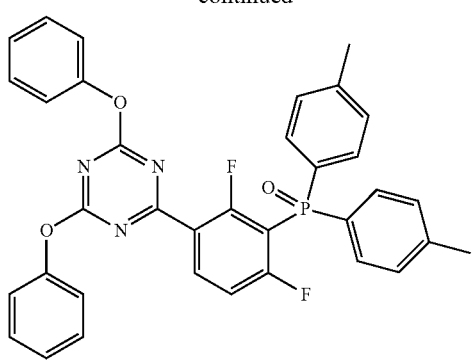
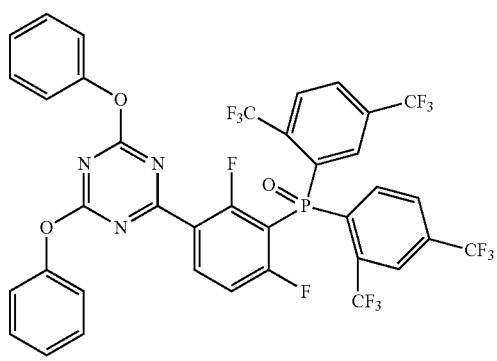
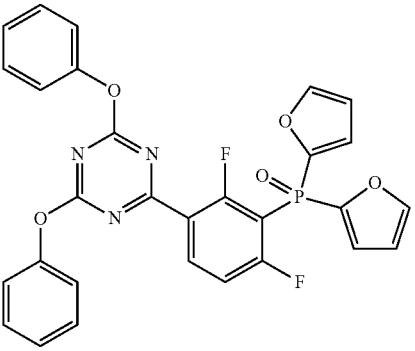
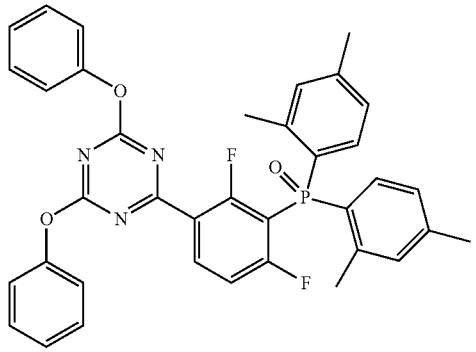

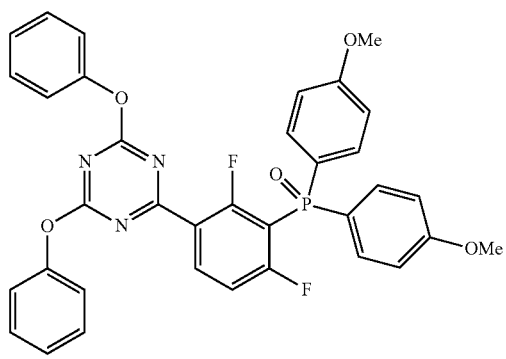
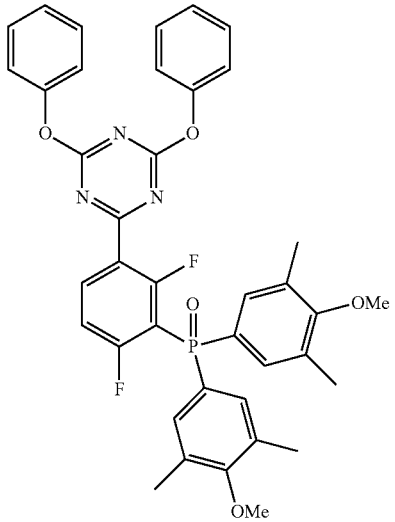
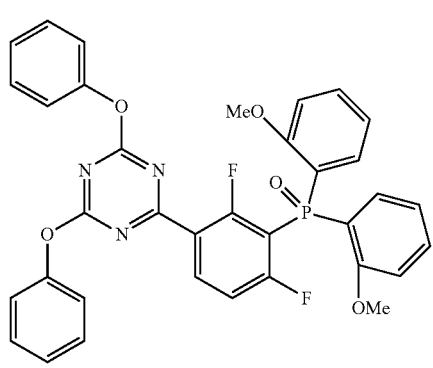
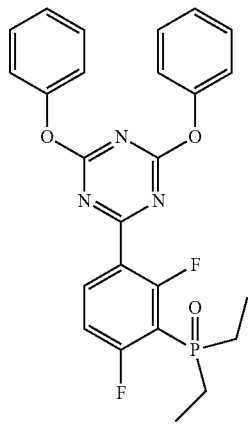
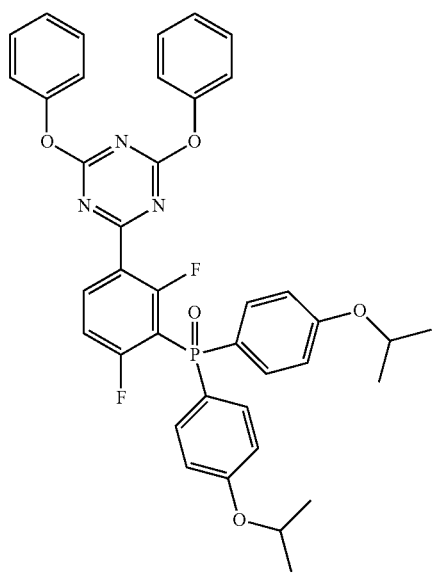
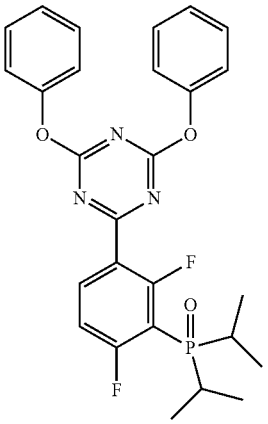

-continued

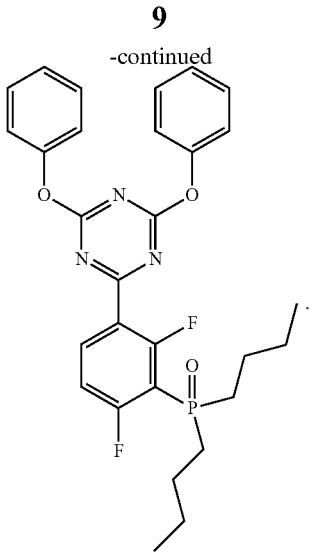

In addition, another embodiment of the present disclosure is directed to providing a novel phosphine oxide functionalized triazine derivative.

In a generally applicable second aspect (i.e., independently combinable with any of the aspects or embodiments identified herein), there is provided a phosphine oxide functionalized triazine derivative represented by Chemical Formula 1 below:

[Chemical Formula 1]

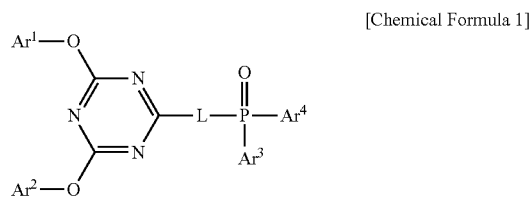

wherein $Ar^1$ and $Ar^2$ can each independently be selected from unsubstituted (C6-C20)aryl and (C6-C20)aryl substituted with fluorine; L can be (C6-C20)arylene substituted with at least one fluorine; and $Ar^3$ and $Ar^4$ can each independently be selected from (C1-C20)alkyl, (C6-C20)aryl, and (C3-C20)heteroaryl, wherein the alkyl, aryl or heteroaryl of $Ar^3$ and $Ar^4$ can be optionally substituted with one or more moieties selected from (C1-C20)alkyl, halo(C1-C20)alkyl, (C1-C20)alkoxy, and halo(C1-C20)alkoxy.

DETAILED DESCRIPTION OF EMBODIMENTS

Figure 1:
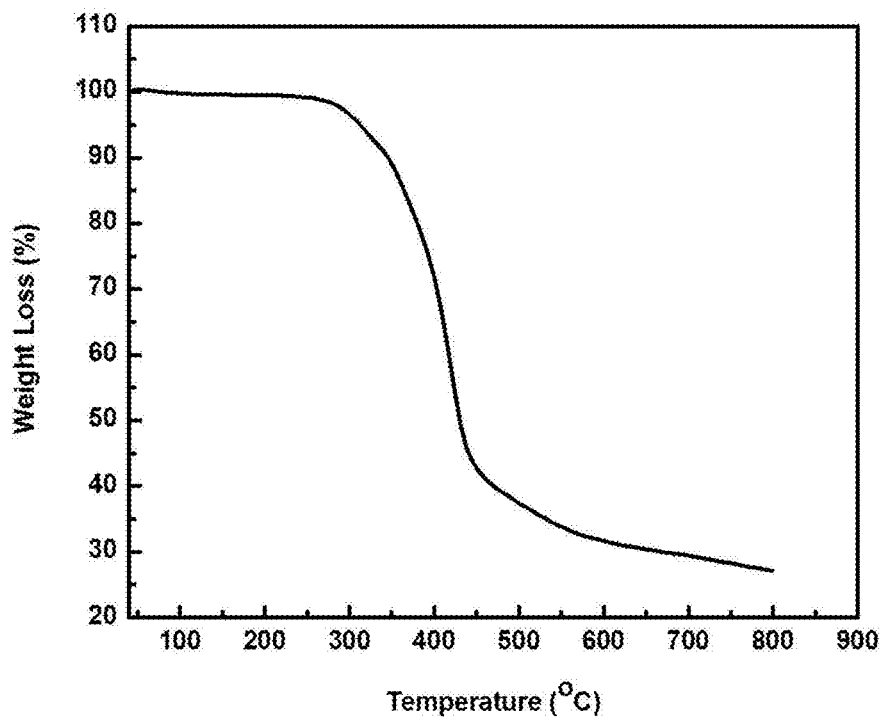
FIG. 1 shows TGA result of PO-TAZ prepared by Example 1.

Hereinafter, the present disclosure will be described in detail. Meanwhile, unless technical and scientific terms used herein are defined otherwise, they have meanings understood by those skilled in the art to which the present disclosure pertains. Known functions and components will be omitted so as not to obscure the description of the present disclosure with unnecessary detail.

The present disclosure relates to an electronic device including a novel structured interface material capable of improving interface properties of the electronic device, and the novel interface material, and more specifically, to an electronic device including the interface material of the present disclosure to allow easy extraction and injection of electrons, thereby exhibiting excellent interface properties, and a phosphine oxide functionalized triazine derivative having a structure in which an electron acceptor phosphine oxide group is substituted in 1,3,5-triazine-based skeleton.

In addition, the present disclosure provides an electronic device including a phosphine oxide functionalized triazine derivative represented by Chemical Formula 1 below as an interface material:

[Chemical Formula 1]

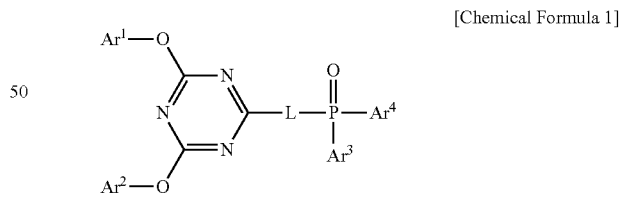

in Chemical Formula 1, $Ar^1$ and $Ar^2$ are each independently (C6-C20)aryl unsubstituted or substituted with fluorine;

L is (C6-C20)arylene substituted with at least one fluorine;

$Ar^3$ and $Ar^4$ are each independently (C1-C20)alkyl, (C6-C20)aryl, or (C3-C20)heteroaryl, wherein the alkyl, aryl, or heteroaryl of $Ar^3$ and $Ar^4$ may be further substituted with at least one selected from (C1-C20)alkyl, halo(C1-C20)alkyl, (C1-C20)alkoxy, and halo(C1-C20)alkoxy; and the heteroaryl includes at least one heteroatom selected from N, O, and S.

In an exemplary embodiment of the present disclosure, the electronic device may be an organic solar cell, a perovskite solar cell, an organic field-effect transistor, an organic thin film transistor, etc.

In an exemplary embodiment of the present disclosure, L may be preferably (C6-C20)arylene substituted with at least two fluorines.

In an exemplary embodiment of the present disclosure, specifically, $Ar^1$ and $Ar^2$ may be each independently phenyl, biphenyl, naphthyl, anthryl, phenanthryl, tetracenyl, pyrenyl, or perylenyl, the phenyl, biphenyl, naphthyl, anthryl, phenanthryl, tetracenyl, pyrenyl, or perylenyl of $Ar^1$ and $Ar^2$ may be further substituted with at least one fluorine; $Ar^3$ and $Ar^4$ may be each independently methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, or pyrazinyl, the methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, or pyrazinyl of $Ar^3$ and $Ar^4$ may be further substituted with at least one selected from methyl, ethyl, propyl, butyl, trifluoromethyl, perfluoroethyl, methoxy, trifluoromethoxy, and perfluoroethoxy.

In an exemplary embodiment of the present disclosure, more preferably, L may be phenylene, biphenylene, naphthylene, anthrylene, phenanthrylene, tetracenylene, pyrenylene, or perylenylene substituted with at least two fluorines.

In an exemplary embodiment of the present disclosure, the phosphine oxide functionalized triazine derivative may be more preferably represented by Chemical Formulas 2 to 4 below:

[Chemical Formula 2]

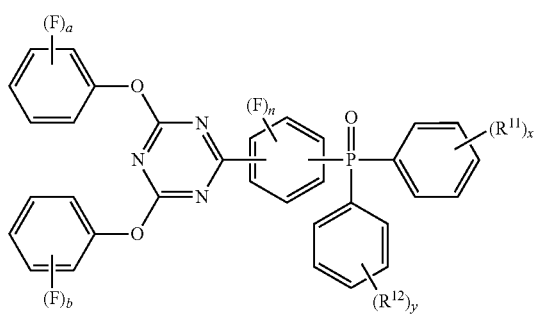

[Chemical Formula 3]

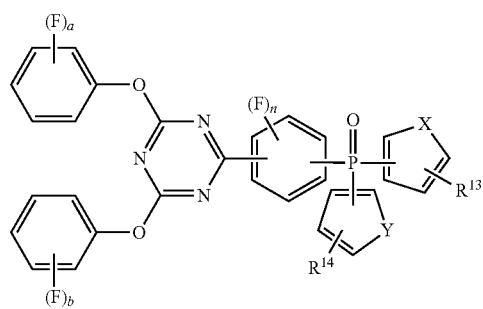

[Chemical Formula 4]

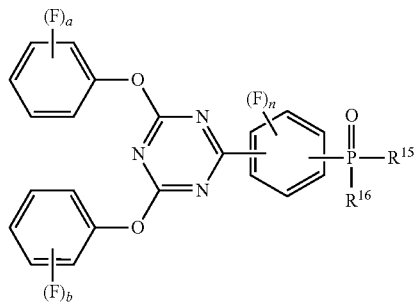

in Chemical Formulas 2 to 4, a and b are each independently an integer from 0 to 5; n is an integer from 2 to 4; $R^{11}$ and $R^{12}$ are each independently (C1-C20)alkyl, halo(C1-C20)alkyl, (C1-C20)alkoxy, or halo(C1-C20)alkoxy; x and y are each independently an integer from 0 to 5; X and Y are each independently NH, O or S; $R^{13}$ and $R^{14}$ are each independently hydrogen, (C1-C20)alkyl, halo(C1-C20)alkyl, (C1-C20)alkoxy, or halo(C1-C20)alkoxy; $R^{15}$ and $R^{16}$ are each independently (C1-C20)alkyl, wherein the alkyl of $R^{15}$ and $R^{16}$ may be further substituted with at least one selected from (C1-C20)alkyl, halo(C1-C20)alkyl, (C1-C20)alkoxy, and halo(C1-C20)alkoxy.

In an exemplary embodiment of the present disclosure, the phosphine oxide functionalized triazine derivative may be selected from the following compounds, but the present disclosure is not limited thereto:

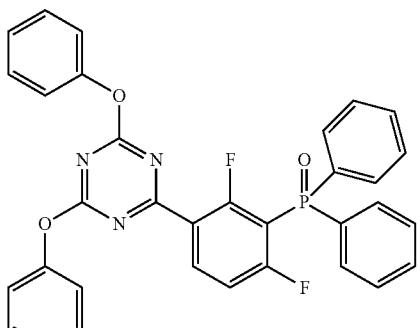

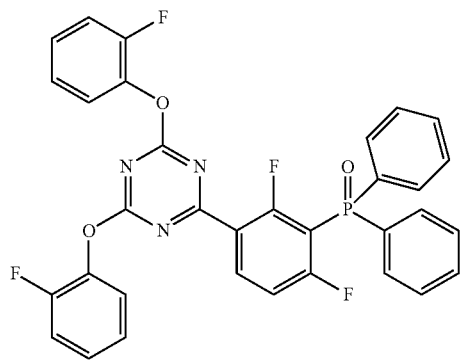

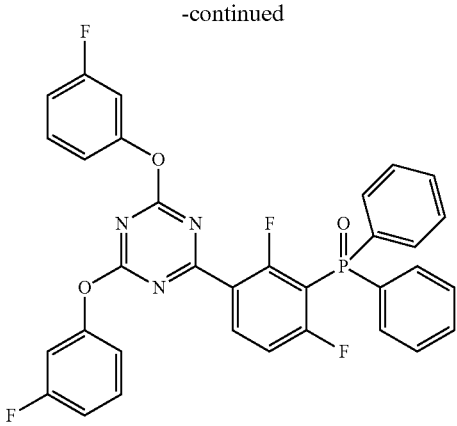
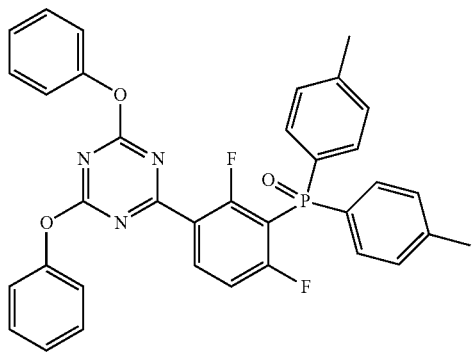
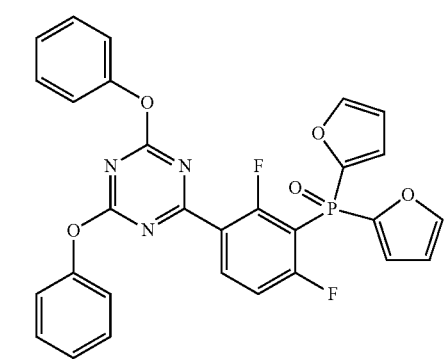
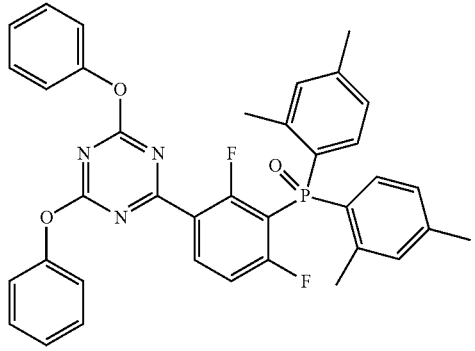

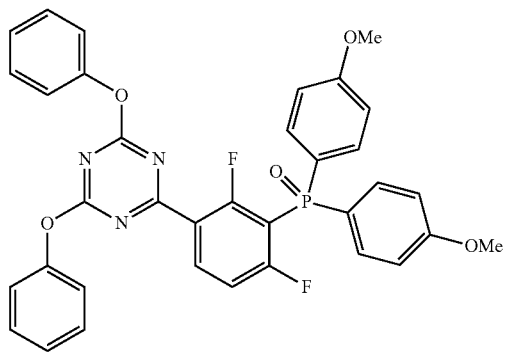
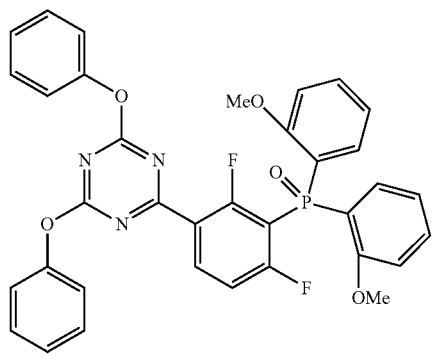
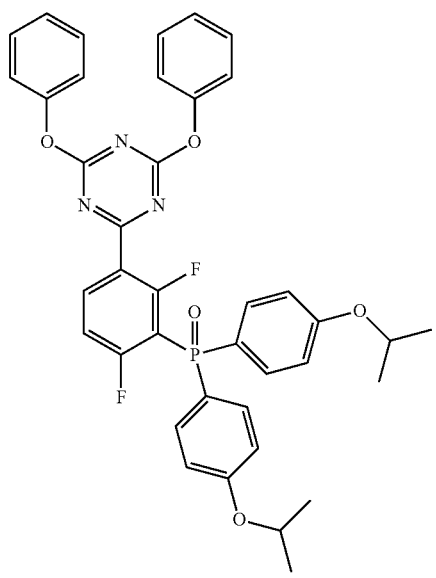
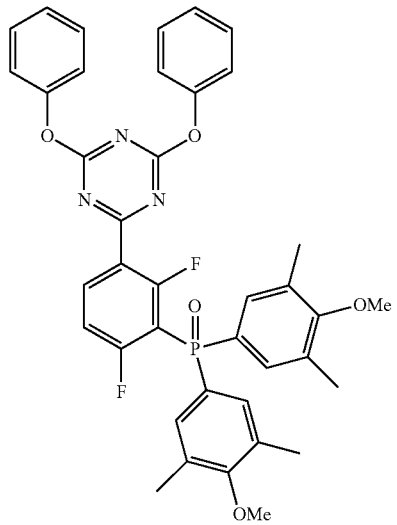
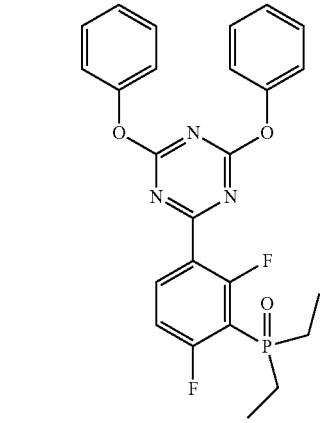
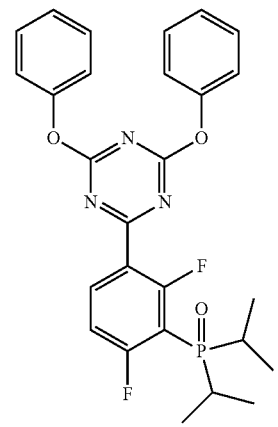

-continued

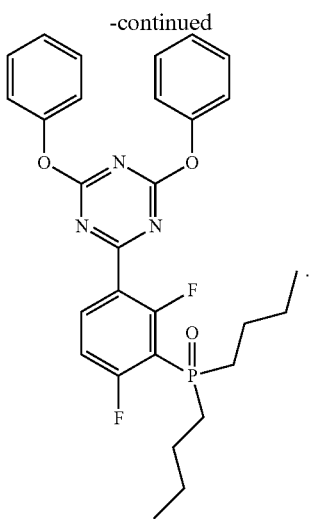

In an exemplary embodiment of the present disclosure, the organic/inorganic hybrid perovskite solar cell includes a first electrode including a conductive transparent substrate; an electron transport layer formed on the first electrode; a light absorption layer formed on the electron transport layer; a hole transport layer formed on the light absorption layer; and a second electrode formed on the hole transport layer, and further includes an interlayer including a phosphine oxide functionalized triazine derivative of the present disclosure between the electron transport layer and the light absorption layer, but is not limited thereto.

The first electrode including the conductive transparent substrate may be a glass substrate or a plastic substrate including a transparent electrode formed of at least one material selected from the group consisting of indium tin oxide (ITO), fluorine tin oxide (FTO), ZnO—$Ga_2O_3$, ZnO—$Al_2O_3$, and tin-based oxides.

The electron transport layer is a metal oxide layer including metal oxide, wherein the metal oxide may be nanoparticle oxides such as titanium dioxide ($TiO_2$), tin dioxide ($SnO_2$), zinc oxide (ZnO), etc., but is not limited thereto.

The light absorption layer is a perovskite layer including a compound having a perovskite crystalline structure, wherein the compounds having a perovskite structure may be one or two or more selected from $H_3NH_3PbI_xCl_y$, (x is a real number satisfying 0≤x≤3, y is a real number satisfying 0≤y≤3, and x+y=3), $CH_3NH_3PbI_xBr_y$, (x is a real number satisfying 0≤x≤3, y is a real number satisfying 0≤y≤3, and x+y=3), $CH_3NH_3PbCl_xBr_y$, (x is a real number satisfying 0≤x≤3, y is a real number satisfying 0≤y≤3, and x+y=3), and $CH_3NH_3PbI_xF_y$, (x is a real number satisfying 0≤x≤3, y is a real number satisfying 0≤y≤3, and x+y=3).

As the second electrode, Au, Ag, Al, etc., may be used. The second electrode may be deposited on the hole transport layer mainly through a thermal-deposition method.

In general, the organic solar cell has a metal/organic semiconductor (photoactive layer)/metal structure (that is, metal-semiconductor or insulator-metal: MSM) structure and includes transparent electrode, indium tin oxide, having a high work function as a cathode, and Al, Ca, or the like, having a low work function as an anode. The hole transport layer may be inserted between the cathode and the photoactive layer and the electron transport layer may be inserted between the anode and the photoactive layer.

The photoactive layer has a bulk-heterojunction structure obtained by mixing electron donors (D) with electron acceptors (A). Since manufacturing method of the photoactive layer is simple, and a surface area at D/A (donor/acceptor) interface is largely increased, possibility of charge separation is increased, and an efficiency in charge collection as electrodes is also increased.

The organic solar cell according to the present disclosure preferably has a BHJ structure. Examples of the electron donors may include P3HT (poly 3-hexylthiophene), PTB7 (Poly[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]), PCPDTBT (poly(2,6-(4,4-bis-(2-ethylhexyl)-4H-cyclopenta[2,1-b;3,4-b]dithiophene)-alt-4,7(2,1,3-benzothiadiazole)), PCPTBT (poly(N-9"-heptadecanyl-2,7-carbazole-alt-5,5-(4',7'-di-2-thienyl-2',1', 3'-benzothiadiazole)), MDMO-PPV (poly[2-methoxy-5-(3', 7'-dimethyloctyloxyl)]-1,4-phenylene vinylene), MEH-PPV (poly[2-methoxy-5-(2"-ethylhexyloxy)-p-phenylene vinylene]), etc. Examples of the electron acceptors may include C60, C70, [60]PCBM (Phenyl $C_{61}$-butyric acid methyl ester), [70]PCBM (Phenyl $C_{71}$-butyric acid methyl ester), [60]ICBA (Indene-$C_{60}$ Bis-Adduct), [60]PCBCR (phenyl-$C_{61}$-butyric acid cholesteryl ester), [70]PCBCR (phenyl-$C_{71}$-butyric acid cholesteryl ester), perylene, PBI (polybenzimidazole), PTCBI (3,4,9,10-perylene-tetracarboxylic bis-benzimidazole), etc. However, the electron donors and the electron acceptors are not limited to the above-described examples.

In a conventional organic solar cell, the electrons are released to the anode, and the holes are released to the cathode, and on the contrary, in an inverted organic solar cell, the electrons are released to the cathode, and the holes are released to the anode. The organic solar cell of the present disclosure includes both of the conventional organic solar cell and the inverted organic solar cell. In general, PEDOT:PSS is mainly used for the hole transport layer of the organic solar cell.

In addition, the present disclosure provides a phosphine oxide functionalized triazine derivative represented by Chemical Formula 1 below:

[Chemical Formula 1]

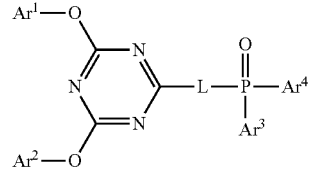

in Chemical Formula 1, $Ar^1$ and $Ar^2$ are each independently (C6-C20)aryl unsubstituted or substituted with fluorine;

L is (C6-C20)arylene substituted with at least one fluorine;

$Ar^3$ and $Ar^4$ are each independently (C1-C20)alkyl, (C6-C20)aryl, or (C3-C20)heteroaryl, wherein the alkyl, aryl, or heteroaryl of $Ar^3$ and $Ar^4$ may be further substituted with at least one selected from (C1-C20)alkyl, halo(C1-C20)alkyl, (C1-C20)alkoxy and halo(C1-C20)alkoxy; and the heteroaryl includes at least one heteroatom selected from N, O, and S.

The phosphine oxide functionalized triazine derivative represented by Chemical Formula 1 of the present disclosure has significantly excellent solubility in alcohols due to the presence of a polar phosphine oxide (P=O) group in the molecular structure, and has a 1,3,5-triazine moiety having excellent electron transport property, such that extraction and injection of electrons for improving interface properties may be easily performed.

The phosphine oxide functionalized triazine derivative according to the present disclosure is prepared by facile protocol with extremely inexpensive 2,4,6-trichloro-1,3,5-triazine as a starting material, which is economical, and has excellent solubility in environmentally friendly solvents such as alcohols as well as compatibility with a large area printing process.

The structure suggested in the present disclosure may introduce various substituents and may control solubility in various solvents including alcohols as well as HOMO and LUMO energy level, by introducing the phosphine oxide, fluorine-based substituents and 1,3,5-triazine derivatives.

Terms: "alkyl" and "alkoxy" described in the present disclosure include both a linear chain type and a branched chain type.

The term "aryl" described herein, which is an organic radical derived from aromatic hydrocarbon due to removal of one hydrogen, includes a single ring system or a fused ring system appropriately including 4 to 7 ring atoms, preferably, 5 or 6 ring atoms in each ring, and even includes a form in which a plurality of aryls are connected by a single bond. Specific examples of the aryl group include aromatic groups such as phenyl, naphthyl, biphenyl, indenyl, fluorenyl, phenanthrenyl, anthracenyl, triphenylenyl, pyrenyl, chrysenyl and naphthacenyl.

The term "arylene" described in the present disclosure is an organic radical derived from aromatic hydrocarbon due to removal of two hydrogens.

The term "heteroaryl" described herein, which means an aryl group including 1 to 4 heteroatoms selected from N, O, and S as an aromatic ring framework atom and carbon as the remaining aromatic ring framework atom, is a 5- to 6-membered monocyclic heteroaryl and a polycyclic heteroaryl condensed with at least one benzene ring. In addition, the heteroaryl in the present disclosure includes even a form in which one or more heteroaryls are connected by a single bond. Examples of the heteroaryl include monocyclic heteroaryls such as furyl, thiophenyl, pyrrolyl, pyranyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and polycyclic heteroaryls such as benzofuranyl, benzothiophenyl, isobenzofuranyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinolizinyl, quinoxalinyl, carbazolyl, phenanthridinyl, benzodioxolyl, etc.

In an exemplary embodiment of the present disclosure, L may be preferably (C6-C20)arylene substituted with at least two fluorines.

In an exemplary embodiment of the present disclosure, specifically, $Ar^1$ and $Ar^2$ may be each independently phenyl, biphenyl, naphthyl, anthryl, phenanthryl, tetracenyl, pyrenyl, or perylenyl, the phenyl, biphenyl, naphthyl, anthryl, phenanthryl, tetracenyl, pyrenyl, or perylenyl of $Ar^1$ and $Ar^2$ may be further substituted with at least one fluorine; $Ar^3$ and $Ar^4$ may be each independently methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, or pyrazinyl, the methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, or pyrazinyl of $Ar^3$ and $Ar^4$ may be further substituted with at least one selected from methyl, ethyl, propyl, butyl, trifluoromethyl, perfluoroethyl, methoxy, trifluoromethoxy, and perfluoroethoxy.

In an exemplary embodiment of the present disclosure, more preferably, L may be phenylene, biphenylene, naphthylene, anthrylene, phenanthrylene, tetracenylene, pyrenylene, or perylenylene substituted with at least two fluorines.

In an exemplary embodiment of the present disclosure, more preferably, the phosphine oxide functionalized triazine derivative may be represented by Chemical Formulas 2 to 4 below:

[Chemical Formula 2]

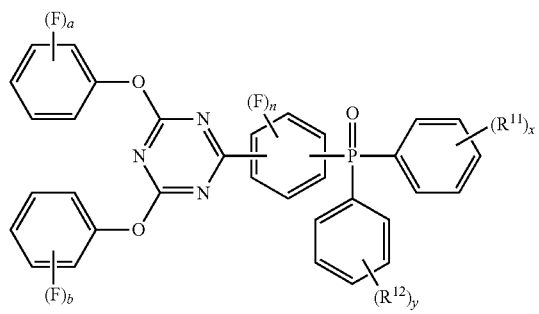

[Chemical Formula 3]

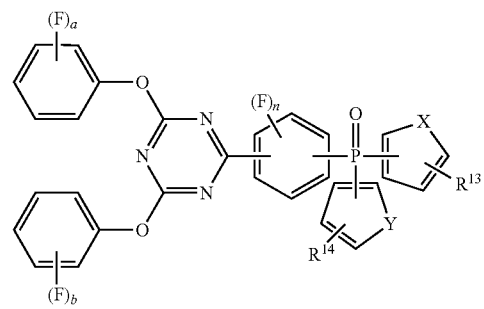

[Chemical Formula 4]

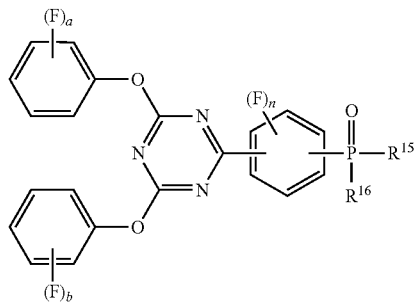

in Chemical Formulas 2 to 4, a and b are each independently an integer from 0 to 5; n is an integer from 2 to 4; $R^{11}$ and $R^{12}$ are each independently (C1-C20)alkyl, halo(C1-C20)alkyl, (C1-C20)alkoxy, or halo(C1-C20)alkoxy; x and y are each independently an integer from 0 to 5; X and Y are each independently NH, O, or S; $R^{13}$ and $R^{14}$ are each independently hydrogen, (C1-C20)alkyl, halo(C1-C20)alkyl, (C1-C20)alkoxy, or halo(C1-C20)alkoxy; $R^{15}$ and $R^{16}$ are each independently (C1-C20)alkyl, wherein the alkyl of $R^{15}$ and $R^{16}$ may be further substituted with at least one selected from (C1-C20)alkyl, halo(C1-C20)alkyl, (C1-C20)alkoxy, and halo(C1-C20)alkoxy.
In an exemplary embodiment of the present disclosure, the phosphine oxide functionalized triazine derivative may be selected from the following compounds, but the present disclosure is not limited thereto:
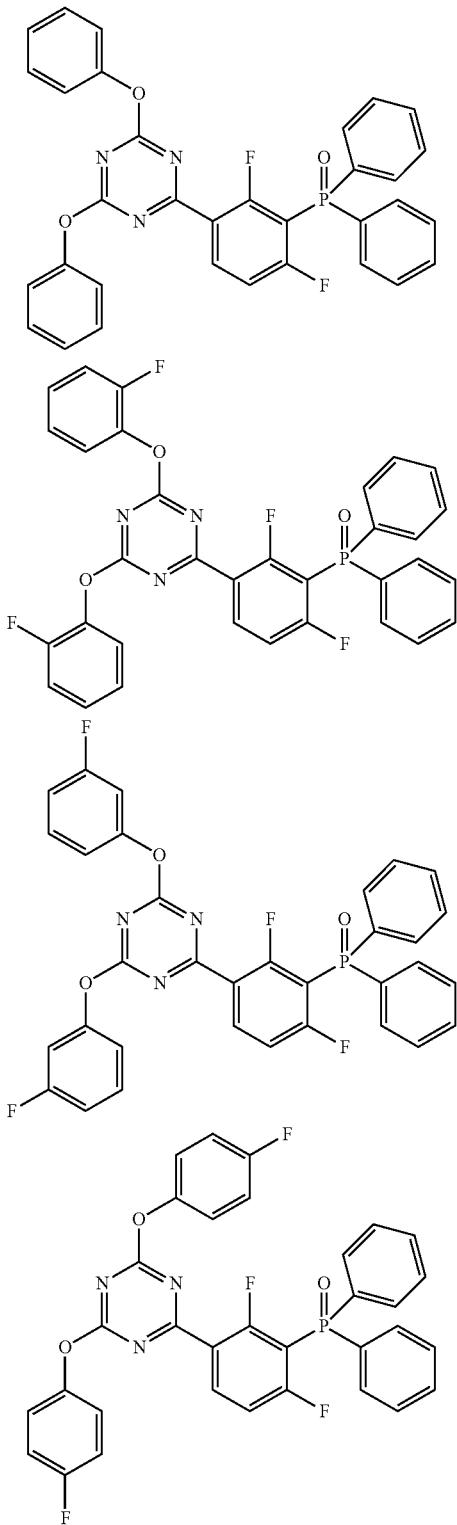
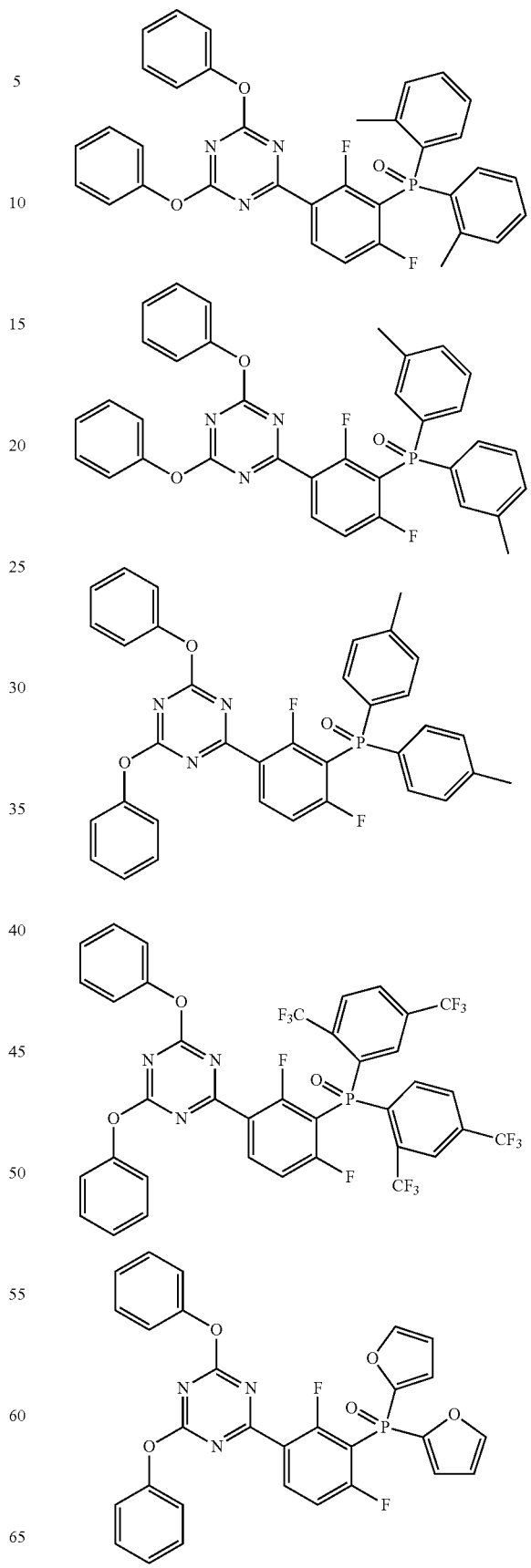

-continued
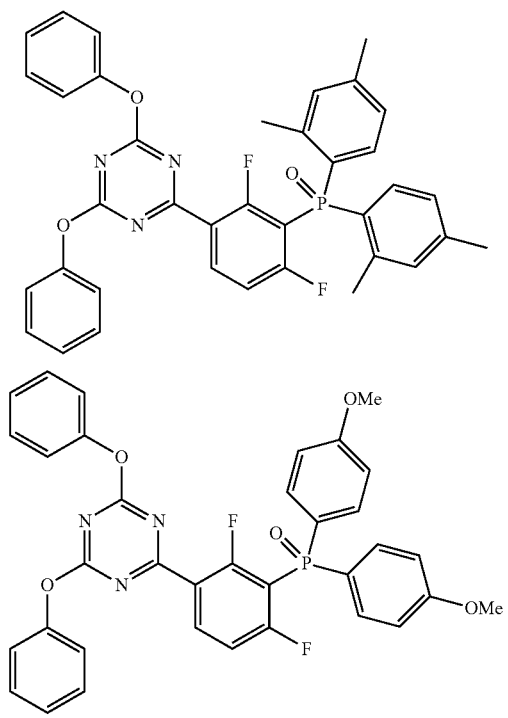
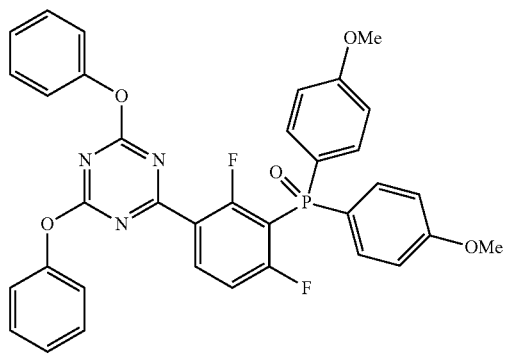
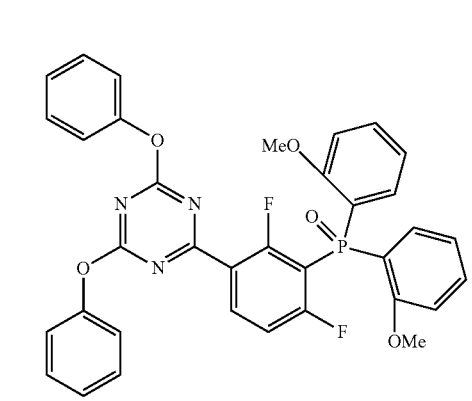
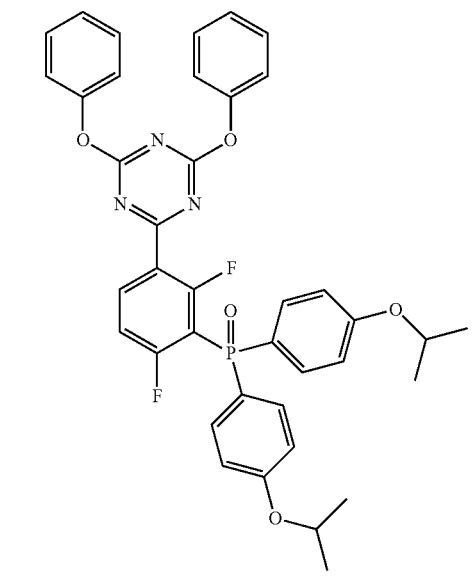
-continued
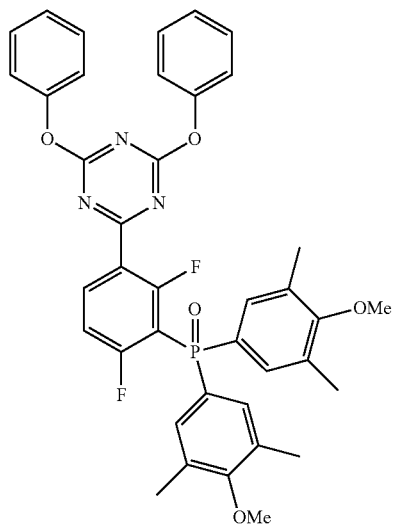
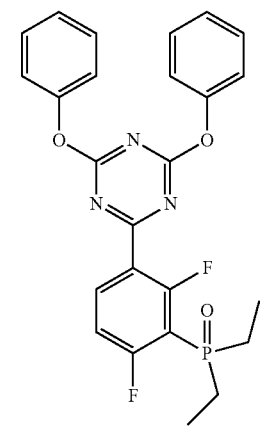
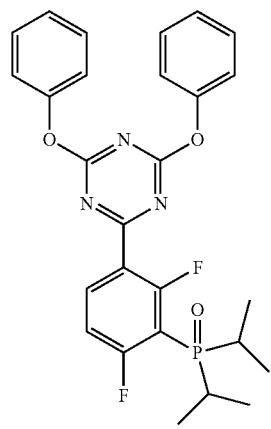

-continued

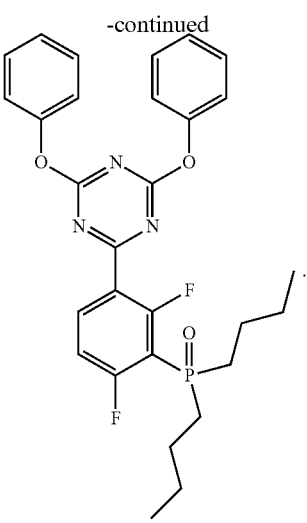

The phosphine oxide functionalized triazine derivative of the present disclosure may be prepared, for example, by Reaction Scheme 1 below. The preparation thereof is described through Examples 1 to 17 in more detail. However, the preparation method of the phosphine oxide functionalized triazine derivative of the present disclosure is not limited to Reaction Scheme 1 below, but may be synthesized by various methods using known organic reactions:

[Reaction Scheme 1]

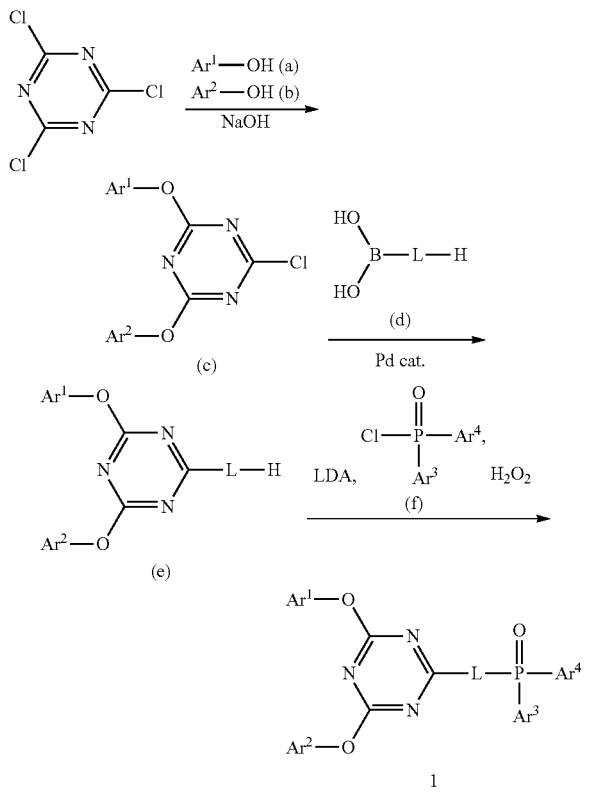

in Reaction Scheme 1, Ar¹ and Ar² are each independently (C6-C20)aryl unsubstituted or substituted with fluorine; L is (C6-C20)arylene substituted with at least one fluorine; and Ar³ and Ar⁴ are each independently (C1-C20)alkyl, (C6-C20)aryl, or (C3-C20)heteroaryl, wherein the alkyl, aryl, or heteroaryl of Ar³ and Ar⁴ may be further substituted with at least one selected from (C1-C20)alkyl, halo(C1-C20)alkyl, (C1-C20)alkoxy, and halo(C1-C20)alkoxy.

The Reaction Scheme 1 includes preparing 2-chloro-4,6-diaryloxy-1,3,5-triazine derivative (Compound c) by reacting cyanuric chloride with phenol derivatives (compounds a and b) in the presence of NaOH (Step 1); preparing a Compound e by palladium-catalyzed cross-coupling reaction of the prepared 2-chloro-4,6-diaryloxy-1,3,5-triazine derivative (Compound c) and an aryl boronic acid derivative substituted with at least one fluorine (Compound d) (Step 2); preparing a phosphine oxide functionalized triazine derivative represented by Chemical Formula 1 through regioselective lithiation of the prepared Compound e, coupling with a chlorodiphenylphosphine derivative (Compound f), and oxidization using hydrogen peroxide (Step 3).

Hereinafter, the present disclosure will be described in detail with reference to Examples. These Examples are provided to help understand the present invention, and the scope of the present disclosure is not construed to be limited to these Examples.

[Example 1] Preparation of PO-TAZ (2-(3-(Diphenylphosphoryl)-2,4-difluorophenyl)-4,6-diphenoxy-1,3,5-triazine)

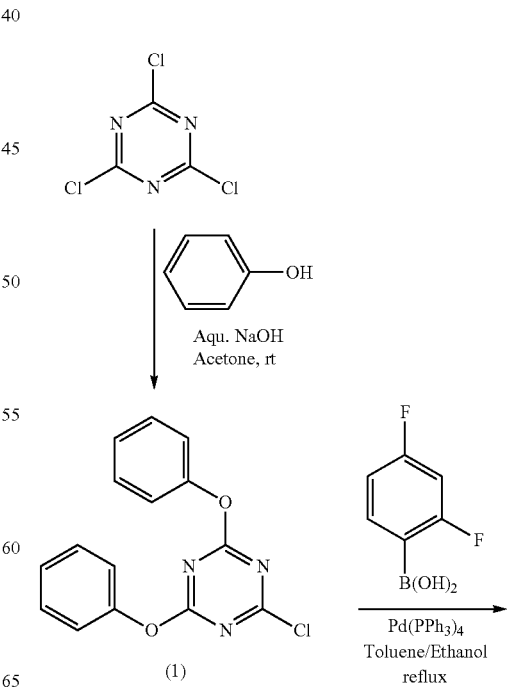

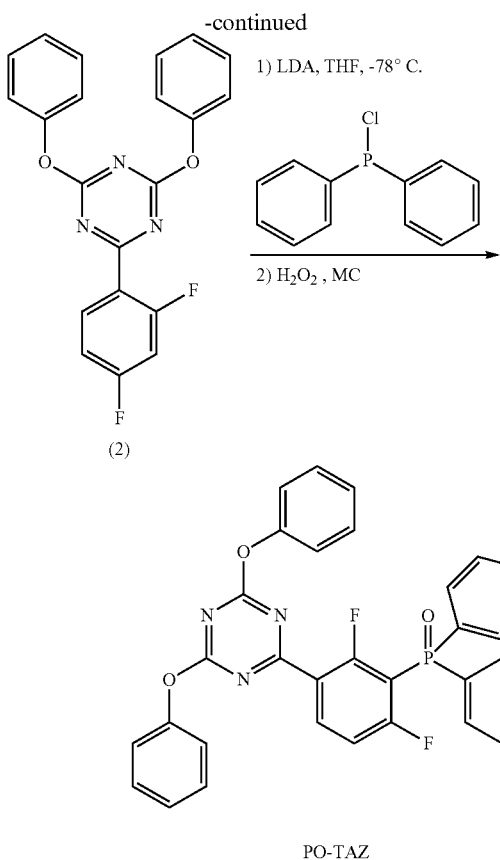

Preparation of 2-Chloro-4,6-diphenoxy-1,3,5-triazine (1)

2,4,6-Trichloro-1,3,5-triazine (cyanuric chloride) (2.5 g, 14 mmol) was dissolved in acetone (200 mL) and cooled to 0° 0. In a different flask, phenol (2.6 g, 28 mmol) was reacted with NaOH (1.1 g, 20 mmol) in water (200 mL) to form a clear aqueous solution. Then, the solution was drop-wise added to the prepared 2,4,6-Trichloro-1,3,5-triazine acetone solution. The mixture was stirred at 0° C. for 12 hours, and water (200 mL) was poured into the mixture to form a white precipitate. The white precipitate was filtered and washed with water and ethanol, and recrystallized with hexane to obtain a white solid, 2-Chloro-4,6-diphenoxy-1,3,5-triazine (1).

Yield: 77%. $^1$H NMR (300 MHz, CDCl$_3$, δ): 7.43 (m, 4H), 7.28 (dd, 2H), 7.14 (m, 4H). $^{13}$C NMR (300 MHz, CDCl$_3$, δ): 121.19, 121.39, 126.09, 126.52, 129.48, 129.69, 151.26, 151.52, 172.39, 173.66, 173.72.

Preparation of 2-(2,4-Difluorophenyl)-4,6-diphenoxy-1,3,5-triazine (2)

Toluene (24 mL), ethanol (12 mL), and 2 M Na$_2$CO$_3$ aqueous solution (15 mL) were added to a mixture of 2-chloro-4,6-diphenoxy-1,3,5-triazine (1 g, 3 mmol), 2,4-difluorophenylboronic acid (0.53 g, 2 mmol), and tetrakis(triphenylphosphine)palladium (0.134 g, 0.2 mmol). The mixture was refluxed under a nitrogen atmosphere for 12 hours, and cooled to room temperature and extracted with dichloromethane, and dried with anhydrous Na$_2$SO$_4$. The solvent was removed under reduced pressure, and residue was purified by silica gel column chromatography (eluent: dichloromethane/hexane=4/1) to obtain a white solid, 2-(2,4-difluorophenyl)-4,6-diphenoxy-1,3,5-triazine (2).

Yield: 58%. $^1$H NMR (300 MHz, CDCl$_3$, δ): 8.24 (m, 1H), 7.45 (t, 4H), 7.28 (m, 6H), 6.92 (m, 2H). $^{13}$C NMR (300 MHz, CDCl$_3$, 5): 105.14, 105.48, 105.81, 111.60, 111.65, 111.88, 111.94, 119.66, 119.72, 119.77, 121.33, 121.38, 121.48, 126.03, 129.10, 129.46, 133.69, 133.72, 133.86, 151.51, 151.66, 161.22, 161.39, 163.85, 164.01, 164.74, 164.90, 167.24, 173.49.

Preparation of 2-(3-(Diphenylphosphoryl)-2,4-difluorophenyl)-4,6-diphenoxy-1,3,5-triazine (PO-TAZ)

2-(2,4-Difluorophenyl)-4,6-diphenoxy-1,3,5-triazine (1.5 g, 4 mmol) was dissolved in THF (30 mL), and a reaction temperature was cooled to −78-C. Lithium diisopropylamide (2M, 2.5 mL) was drop-wise added to the reaction mixture, and stirred at the same temperature for 1 hour. Then, chlorodiphenylphosphine (1.1 g, 5 mmol) (2 mL) was added to the mixture, and stirred overnight, and the reaction was quenched by adding water thereto. The obtained mixture was extracted with ethyl acetate (EA) and dried with anhydrous Na$_2$SO$_4$. After removing the solvent, the residue was diluted with CH$_2$Cl$_2$ (30 mL) and hydrogen peroxide (30%) (20 mL) and then stirred at room temperature for 3 hours. The crude product was extracted with chloroform and purified by silica gel column chromatography (eluent: EA) to obtain a white solid, 2-(3-(diphenylphosphoryl)-2,4-difluorophenyl)-4,6-diphenoxy-1,3,5-triazine (PO-TAZ).

Yield: 72%. $^1$H NMR (300 MHz, CDCl$_3$, δ): 8.24 (m, 1H), 7.74 (m, 4H), 7.59-7.42 (m, 6H), 7.34 (m, 4H), 7.21 (m, 2H), 7.16 (d, 4H), 6.98 (m, 1H). MS (EI, m/z): [M]+calcd for C$_{33}$H$_{22}$F$_2$N$_3$O$_3$P, 577.52; found, 578.14. $^{13}$C NMR (300 MHz, CDCl$_3$, δ): 111.25, 112.45, 112.95, 113.27, 120.73, 120.79, 120.87, 121.35, 126.05, 128.56, 128.73, 129.46, 131.10, 131.24, 131.88, 132.24, 132.27, 133.36, 137.71, 137.75, 127.87, 151.52, 161.16, 161.27, 164.74, 164.85, 164.96, 168.33, 168.43, 172.54, 172.98, 173.06.

[Examples 2 to 4] Preparation of F PO-TAZ Derivative Introduced with Fluorine Substituent

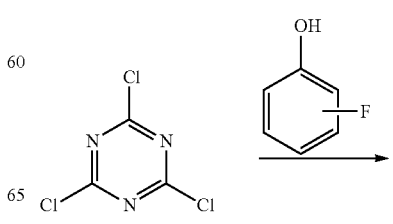

29
-continued

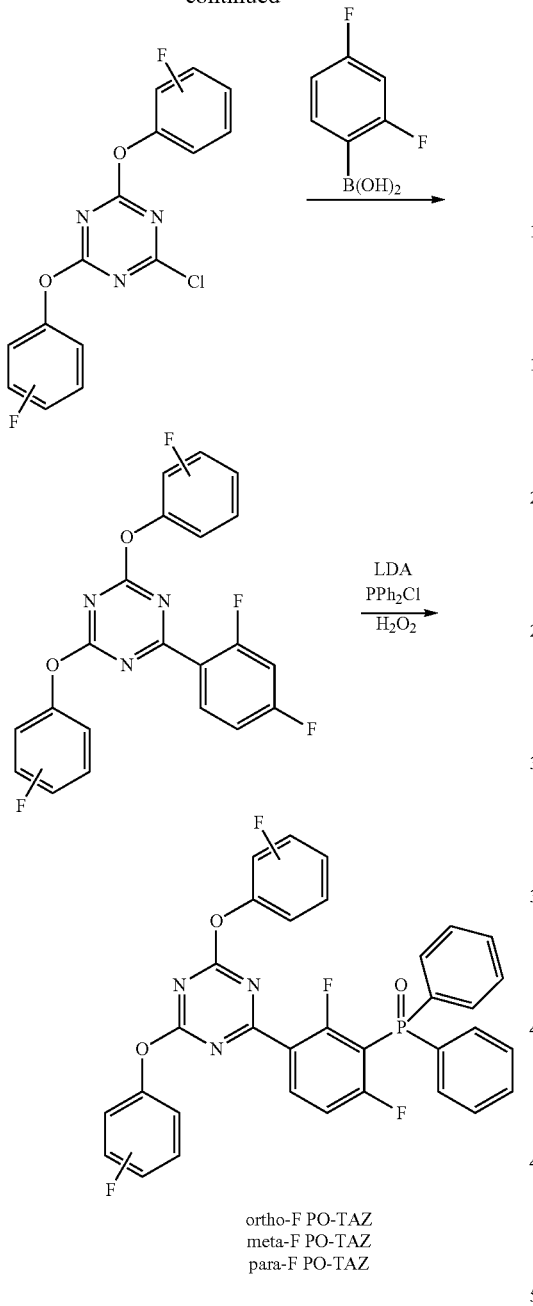

ortho-F PO-TAZ
meta-F PO-TAZ
para-F PO-TAZ

Ortho-F PO-TAZ (Example 2), meta-F PO-TAZ (Example 3) and para-F PO-TAZ (Example 4) were obtained by performing the reaction in the same manner as in Example 1 except for using 2-fluorophenol, 3-fluorophenol or 4-fluorophenol, respectively, instead of using phenol in Example 1.

Ortho-F PO-TAZ (Example 2) $^1$H NMR (300 MHz, CDCl$_3$, δ): 8.24 (m, 1H), 7.80-7.62 (m, 4H), 7.60-7.52 (m, 2H), 7.50-7.48 (m, 4H), 7.12-6.84 (9H).

Meta-F PO-TAZ (Example 3) $^1$H NMR (300 MHz, CDCl$_3$, δ): 8.32-8.24 (m, 1H), 7.72-7.86 (m, 4H), 7.64-7.54 (m, 2H), 7.52-7.42 (m, 4H), 7.38-7.28 (m, 3H), 7.08-6.88 (m, 6H).

Para-F PO-TAZ (Example 4) $^1$H NMR (300 MHz, CDCl$_3$, δ): 8.24 (m, 1H), 7.80-7.62 (m, 4H), 7.60-7.48 (m, 6H), 7.12-6.84 (9H).

30

[Example 5] Preparation of 2-(3-(di(o-tolyl)phosphoryl)-2,4-difluorophenyl)-4,6-diphenoxy-1,3,5-triazine (Compound A)

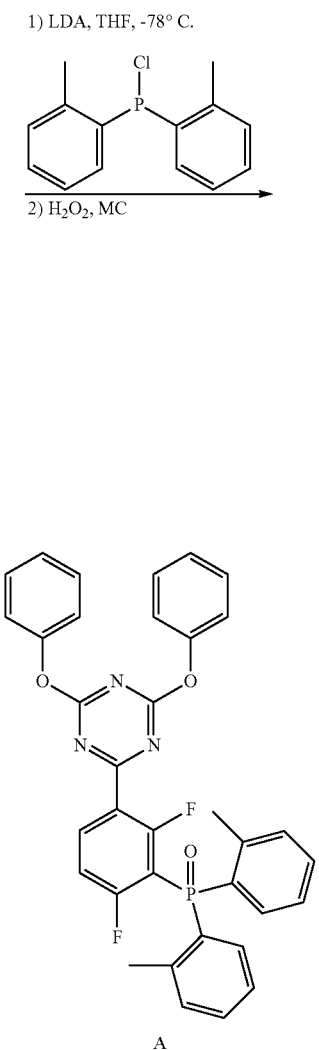

2-(3-(Di(o-tolyl)phosphoryl)-2,4-difluorophenyl)-4,6-diphenoxy-1,3,5-triazine (Compound A) was obtained by performing the reaction in the same manner as in Example 1 except for using chloro di-o-tolylphosphine instead of using chlorodiphenylphosphine in Example 1.

Yield: 70%, $^1$H NMR (300 MHz, CDCl$_3$, δ ppm): 7.78 (d, 1H), 7.75 (d, 1H), 7.64 (d, 2H), 7.3-6.9 (m, 16H), 2.34 (m, 6H).

[Example 6] Preparation of 2-(3-(Di(m-tolyl)phosphoryl)-2,4-difluorophenyl)-4,6-diphenoxy-1,3,5-triazine (Compound B)

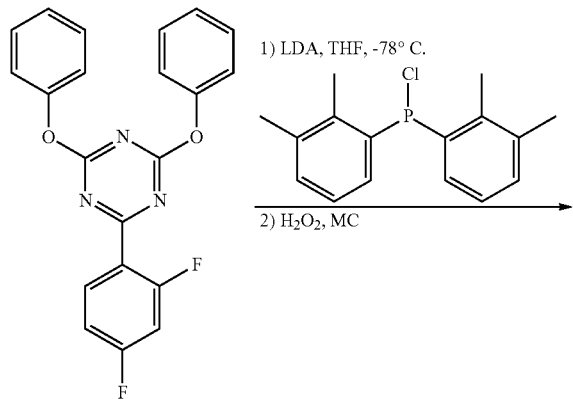

(2)

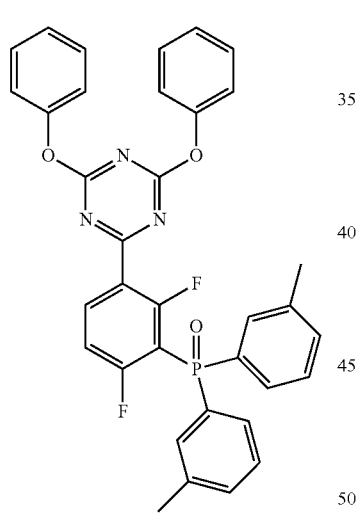

B 2-(3-(Di(m-tolyl)phosphoryl)-2,4-difluorophenyl)-4,6-diphenoxy-1,3,5-triazine (Compound B) was obtained by performing the reaction in the same manner as in Example 1 except for using chloro di-m-tolylphosphine instead of using chlorodiphenylphosphine in Example 1.

Yield: 70%, $^1$H NMR (300 MHz, CDCl$_3$, δ ppm): 7.78 (d, 1H), 7.75 (d, 1H), 7.64 (m, 4H), 7.3-6.9 (m, 14H), 2.34 (m, 6H).

[Example 7] Preparation of 2-(3-(Di(p-tolyl)phosphoryl)-2,4-difluorophenyl)-4,6-diphenoxy-1,3,5-triazine (Compound C)

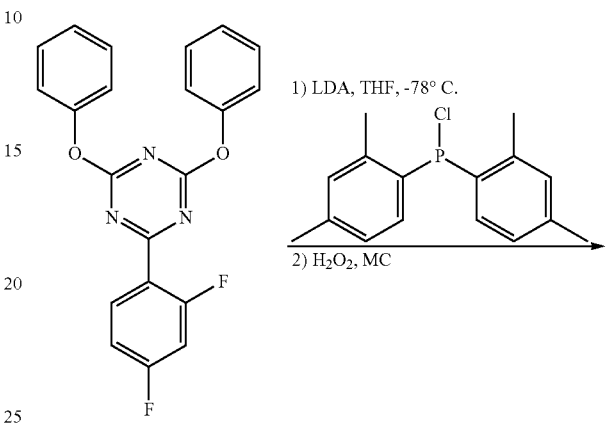

(2)

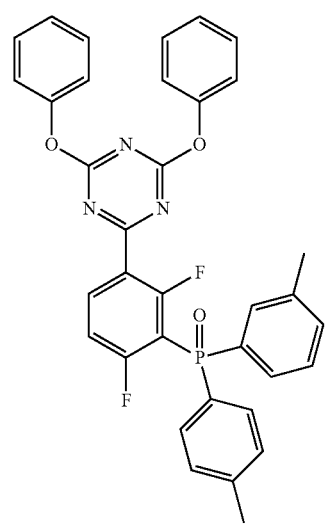

C 2-(3-(Di(p-tolyl)phosphoryl)-2,4-difluorophenyl)-4,6-diphenoxy-1,3,5-triazine (Compound C) was obtained by performing the reaction in the same manner as in Example 1 except for using chloro di-p-tolylphosphine instead of using chlorodiphenylphosphine in Example 1.

Yield: 70%, $^1$H NMR (300 MHz, CDCl$_3$, δ ppm): 7.78 (d, 1H), 7.66 (m, 4H), 7.28-7.20 (m, 8H), 7.09-7.01 (dt, 3H), 6.98 (m, 4H), 2.34 (m, 6H).

[Example 8] Preparation of 2-(3-(Di(bis(2,4-bis(trifluoromethyl)phenyl))phosphoryl)-2,4-difluorophenyl)-4,6-diphenoxy-1,3,5-triazine (Compound D)

[Example 9] Preparation of 2-(3-(Di(furyl))phosphoryl)-2,4-difluorophenyl)-4,6-diphenoxy-1,3,5-triazine (Compound E)

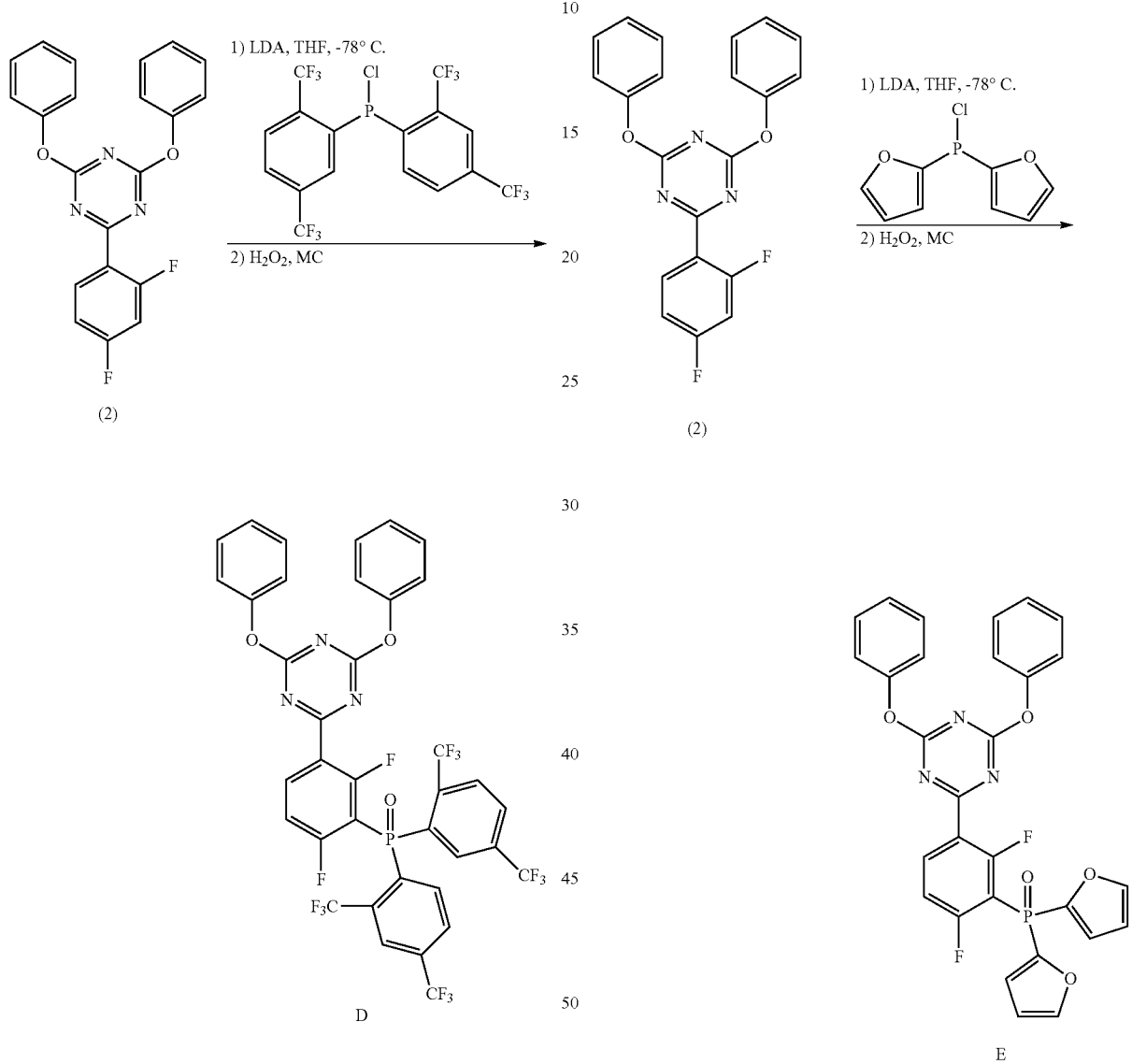

2-(3-(Di(bis(2,4-bis(trifluoromethyl)phenyl))phosphoryl)-2,4-difluorophenyl)-4,6-diphenoxy-1,3,5-triazine (Compound D) was obtained by performing the reaction in the same manner as in Example 1 except for using (2,4-bis(trifluoromethyl)phenyl) (2,5-bis(trifluoromethyl)phenyl) chlorophosphine instead of using chlorodiphenylphosphine in Example 1.

Yield: 70%, $^1$H NMR (300 MHz, CDCl$_3$, δ ppm): 7.88 (s, 2H), 7.78 (d, 1H), 7.69-7.61 (m, 4H), 7.28-7.20 (m, 4H), 7.09-7.01 (dt, 3H), 6.98 (m, 4H)

2-(3-(Di(furyl))phosphoryl)-2,4-difluorophenyl)-4,6-diphenoxy-1,3,5-triazine (Compound E) was obtained by performing the reaction in the same manner as in Example 1 except for using chlorodifuran-2-ylphosphine instead of using chlorodiphenylphosphine in Example 1.

Yield: 70%, $^1$H NMR (300 MHz, CDCl$_3$, δ ppm): 7.78-7.72 (m, 3H), 7.28-7.20 (m, 4H), 7.10 (m, 2H), 7.09-7.01 (dt, 3H), 6.98 (m, 4H), 6.63 (t, 2H).

[Example 10] Preparation of 2-(3-(Di(2,4-dimethyl-phenyl)phosphoryl)-2,4-difluorophenyl)-4,6-diphenoxy-1,3,5-triazine (Compound F)

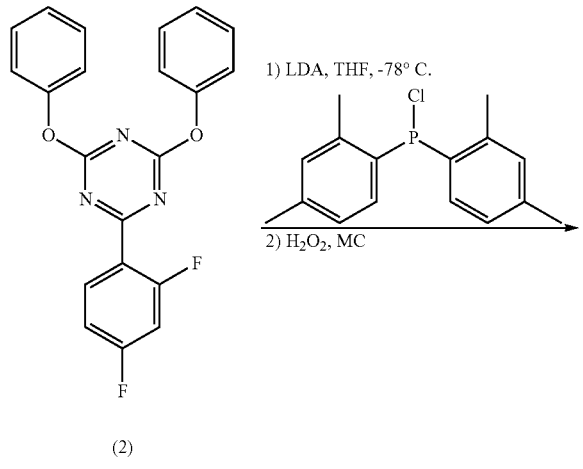

(2)

[Example 11] Preparation of 2-(3-(Di(4-methoxyphenyl)phosphoryl)-2,4-difluorophenyl)-4,6-diphenoxy-1,3,5-triazine (Compound G)

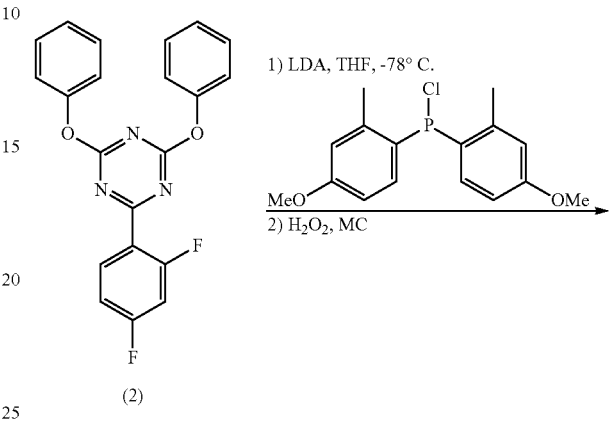

(2)

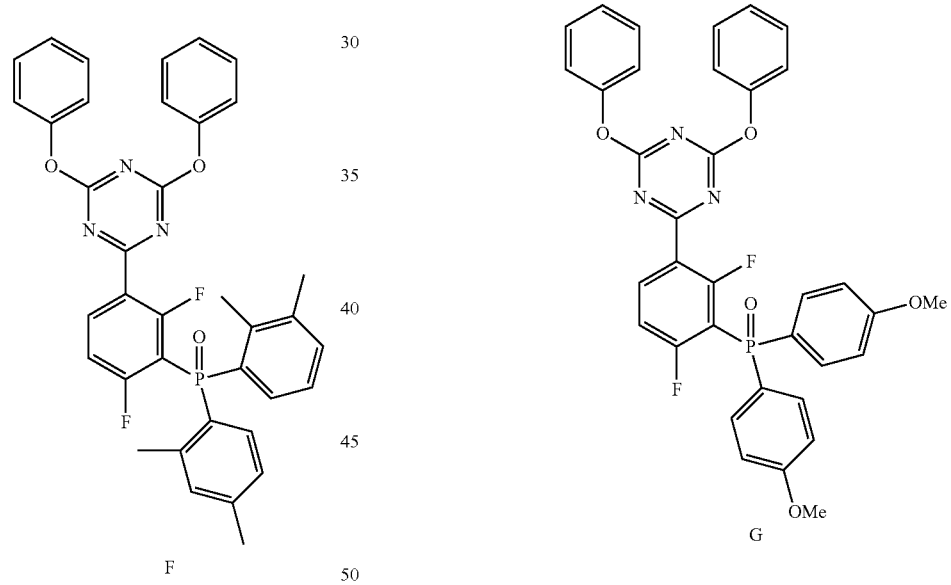

2-(3-(Di(2,4-dimethylphenyl)phosphoryl)-2,4-difluorophenyl)-4,6-diphenoxy-1,3,5-triazine (Compound F) was obtained by performing the reaction in the same manner as in Example 1 except for using chlorobis(2,4-dimethylphenyl)phosphine instead of using chlorodiphenylphosphine in Example 1.

Yield: 70%, $^1$H NMR (300 MHz, CDCl$_3$, δ ppm): 7.78 (m, 1H), 7.58 (m, 2H), 7.28-7.20 (m, 4H), 7.10 (m, 2H), 7.09-7.01 (dt, 5H), 6.98 (m, 4H), 2.34 (s, 6H).

2-(3-(Di(4-methoxyphenyl)phosphoryl)-2,4-difluorophenyl)-4,6-diphenoxy-1,3,5-triazine (Compound G) was obtained by performing the reaction in the same manner as in Example 1 except for using chlorobis(4-methoxyphenyl) phosphine instead of using chlorodiphenylphosphine in Example 1.

Yield: 70%, $^1$H NMR (300 MHz, CDCl$_3$, δ ppm): 7.78 (m, 1H), 7.68-7.64 (m, 4H), 7.28-7.20 (m, 4H), 7.09-7.01 (dt, 3H), 6.99 (m, 4H), 6.84 (d, 4H), 3.94 (s, 6H)

[Example 12] Preparation of 2-(3-(Di(2-methoxyphenyl)phosphoryl)-2,4-difluorophenyl)-4,6-diphenoxy-1,3,5-triazine (Compound H)

[Example 13] Preparation of 2-(3-(Di(4-isopropoxyphenyl))phosphoryl)-2,4-difluorophenyl)-4,6-diphenoxy-1,3,5-triazine (Compound I)

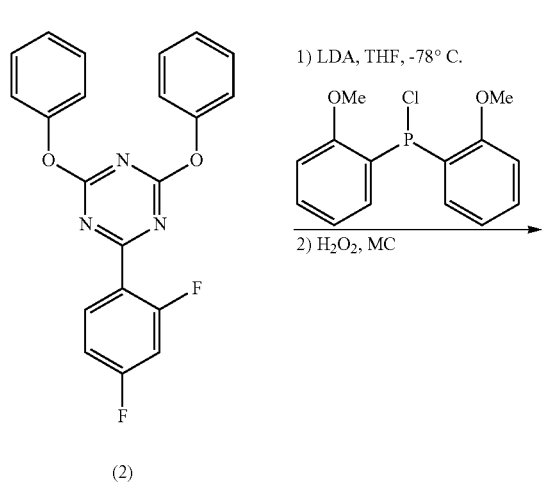

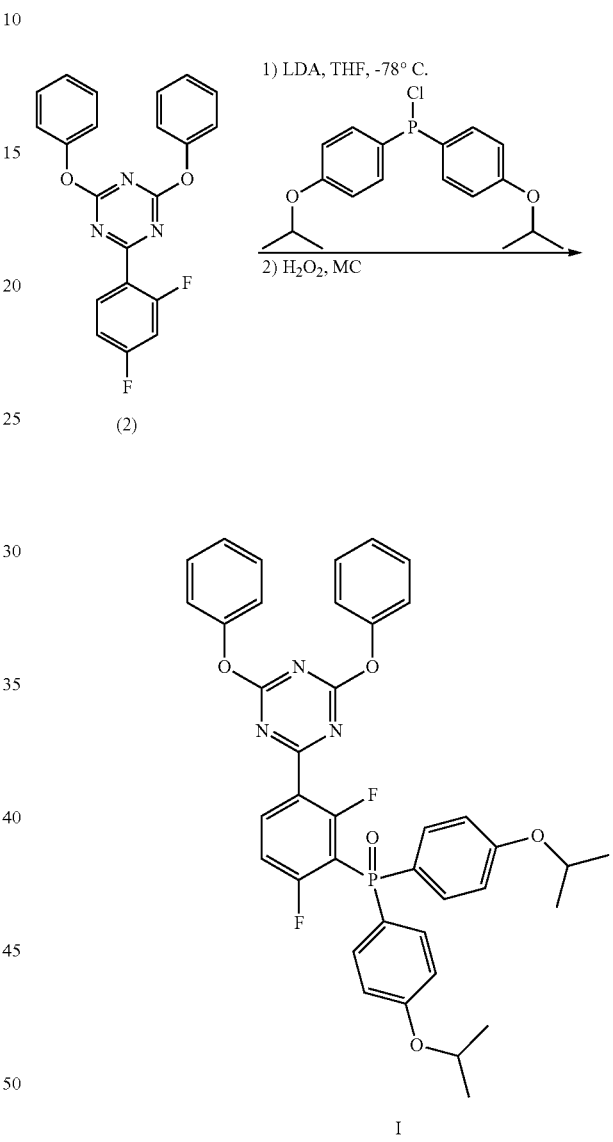

2-(3-(Di(2-methoxyphenyl)phosphoryl)-2,4-difluorophenyl)-4,6-diphenoxy-1,3,5-triazine (Compound H) was obtained by performing the reaction in the same manner as in Example 1 except for using chlorobis(2-methoxyphenyl)phosphine instead of using chlorodiphenylphosphine in Example 1.

Yield: 70%, $^1$H NMR (300 MHz, CDCl$_3$, δ ppm): 7.78 (m, 1H), 7.70-7.64 (m, 2H), 7.39 (m, 2H), 7.28-7.20 (m, 4H), 7.09-7.01 (dt, 5H), 6.99-6.90 (m, 6H), 3.94 (s, 6H).

2-(3-(Di(4-isopropoxyphenyl))phosphoryl)-2,4-difluorophenyl)-4,6-diphenoxy-1,3,5-triazine (Compound I) was obtained by performing the reaction in the same manner as in Example 1 except for using chlorobis(4-isopropoxyphenyl)phosphine instead of using chlorodiphenylphosphine in Example 1.

Yield: 70%, $^1$H NMR (300 MHz, CDCl$_3$, δ ppm): 7.78 (m, 1H), 7.66 (m, 4H), 7.28-7.20 (m, 4H), 7.09-7.01 (dt, 3H), 6.99-6.92 (m, 8H), 4.82 (s, 2H), 1.38 (d, 12H).

[Example 14] Preparation of 2-(3-(Di(4-methoxy-3,5-dimethylphenyl)phosphoryl)-2,4-difluorophenyl)-4,6-diphenoxy-1,3,5-triazine (Compound J)

[Example 15] Preparation of 2-((3-(Diethyl)-phosphoryl)-2,4-difluorophenyl)-4,6-diphenoxy-1,3,5-triazine (Compound K)

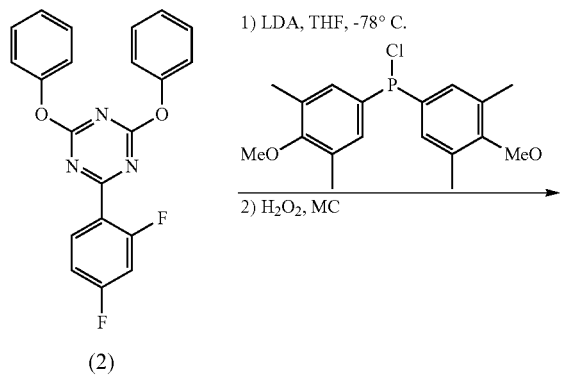

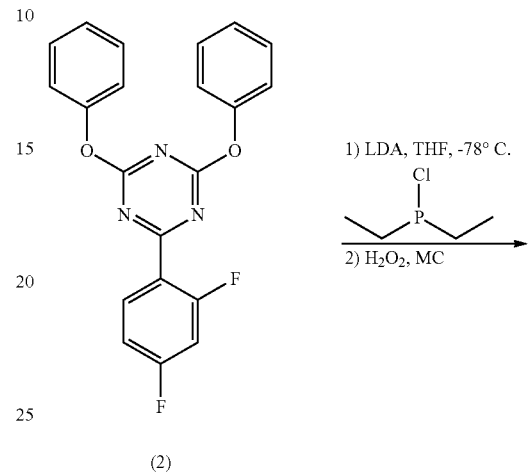

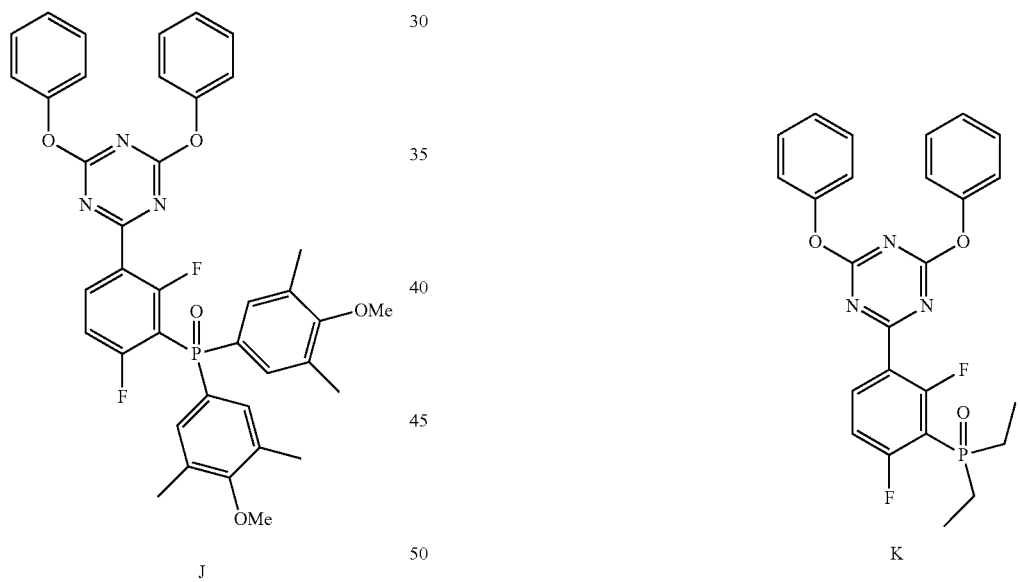

2-(3-(Di(4-methoxy-3,5-dimethylphenyl)phosphoryl)-2,4-difluorophenyl)-4,6-diphenoxy-1,3,5-triazine (Compound J) was obtained by performing the reaction in the same manner as in Example 1 except for using chlorobis(4-methoxy-3,5-dimethylphenyl)phosphine instead of using chlorodiphenylphosphine in Example 1.

Yield: 70%, $^1$H NMR (300 MHz, CDCl$_3$, δ ppm): 7.78 (m, 1H), 7.28-7.20 (m, 4H), 7.09-7.01 (dt, 3H), 6.99-6.92 (m, 8H), 3.94 (s, 6H), 2.15 (d, 12H).

2-((3-(Diethyl)-phosphoryl)-2,4-difluorophenyl)-4,6-diphenoxy-1,3,5-triazine (Compound K) was obtained by performing the reaction in the same manner as in Example 1 except for using chlorodiethylphosphine instead of using chlorodiphenylphosphine in Example 1.

Yield: 70%, $^1$H NMR (300 MHz, CDCl$_3$, δ ppm): 7.78 (m, 1H), 7.28-7.20 (m, 4H), 7.09-7.01 (dt, 3H), 6.99-6.92 (m, 4H), 1.92 (t, 4H), 1.14 (d, 6H).

[Example 16] Preparation of 2-((3-(Diisopropyl)-phosphoryl)-2,4-difluorophenyl)-4,6-diphenoxy-1,3,5-triazine (Compound L)

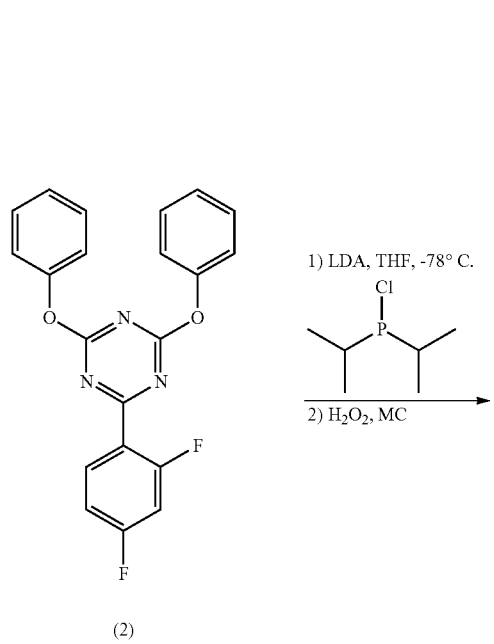

(2)

L 2-((3-(Diisopropyl)-phosphoryl)-2,4-difluorophenyl)-4,6-diphenoxy-1,3,5-triazine (Compound L) was obtained by performing the reaction in the same manner as in Example 1 except for using chlorodiisopropylphosphine instead of using chlorodiphenylphosphine in Example 1.

Yield: 70%, 1H NMR (300 MHz, CDCl₃, δ ppm): 7.76 (m, 1H), 7.28-7.20 (m, 4H), 7.09-7.01 (dt, 3H), 6.99-6.92 (m, 4H), 3.69 (m, 2H), 1.08 (d, 12H).

[Example 17] Preparation of 2-((3-(Dibutyl)-phosphoryl)-2,4-difluorophenyl)-4,6-diphenoxy-1,3,5-triazine (Compound M)

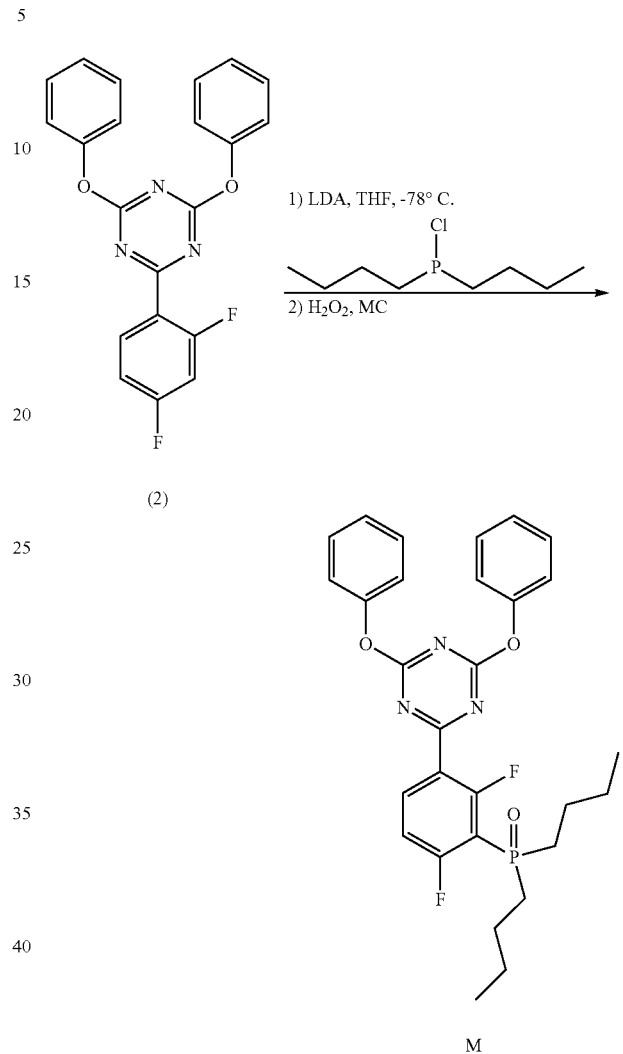

(2)

M 2-((3-(Dibutyl)-phosphoryl)-2,4-difluorophenyl)-4,6-diphenoxy-1,3,5-triazine (Compound M) was obtained by performing the reaction in the same manner as in Example 1 except for using dibutylchlorophosphine instead of using chlorodiphenylphosphine in Example 1.

Yield: 70%, $^1$H NMR (300 MHz, CDCl₃, δ ppm): 7.76 (m, 1H), 7.28-7.20 (m, 4H), 7.09-7.01 (dt, 3H), 6.99-6.92 (m, 4H), 1.82 (t, 4H), 1.66 (p, 4H), 1.42 (m, 4H), 0.94 (t, 6H).

[Example 18] Manufacture of COSC (Conventional Organic Solar Cell)

An indium tin oxide (ITO)-coated glass substrate was cleaned by sonication in acetone, detergent, deionized water, and isopropanol to remove impurities, and dried in an oven, followed by plasma treatment.

A thin hole-collection layer (ca. 35 nm) of PEDOT:PSS (poly(3,4-ethylenedioxythiophene):poly(styrenesulfonate)) (Clevios P VP AI 4083, filtered at 0.45 μm) was spin-coated on the pre-cleaned ITO-coated glass substrates and baked at 140° C. for 15 min under ambient conditions.

Poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7) and 1-(2-methoxycarbonly)-propyl-11-phenyl-(6,6)C71 (PC$_{71}$BM) were used for the photoactive layer. PTB7 (8 mg) and PC$_{71}$BM (12 mg) were dissolved in CB (chlorobenzene, 1 mL) and DIO (1,8-diiodooctane, 3 wt %), followed by spin-coating on the PEDOT:PSS hole-collection layer, and drying at room temperature for 30 minutes, to form a photoactive layer having a thickness of 100 nm.

The PO-TAZ (0.05 mg) prepared by Example 1 was dissolved in isopropanol (1 mL), followed by spin-coating on the photoactive layer, to form a PO-TAZ layer having a thickness of 5 nm.

An aluminum electrode covered with a mask was thermal-deposited at a thickness of 100 nm under $10^{-7}$ Torr in a vacuum chamber.

Figure 4:
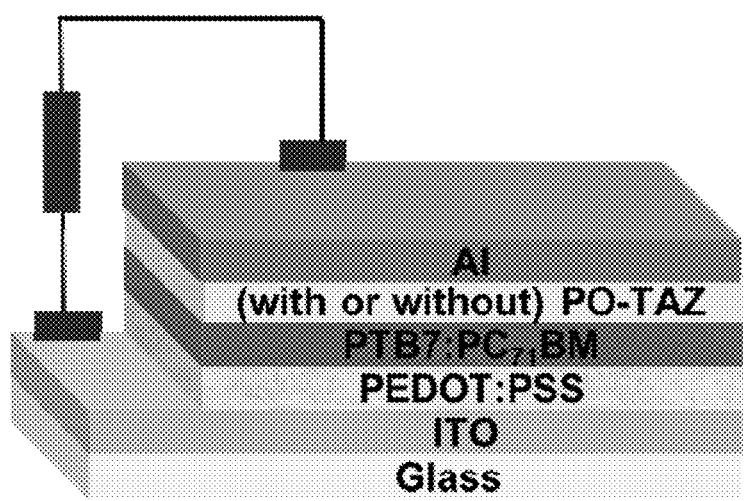
FIG. 4 shows a structure of COSC manufactured by Example 18.
Figure 5:
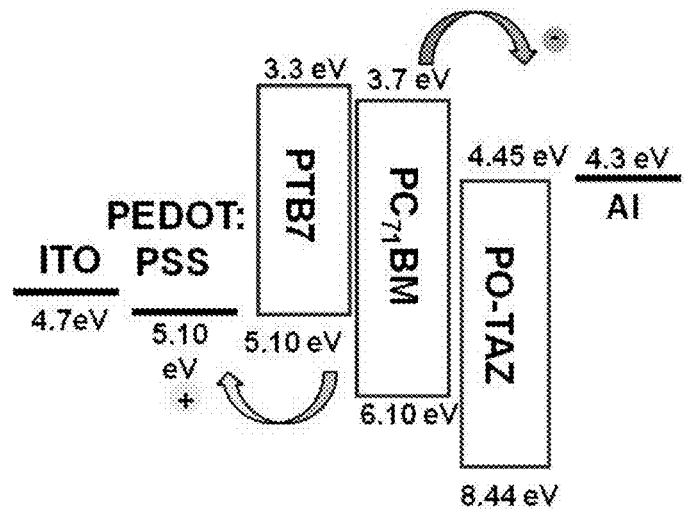
FIG. 5 shows a HOMO LUMO energy level diagram of COSC manufactured by Example 18.
Figure 6:
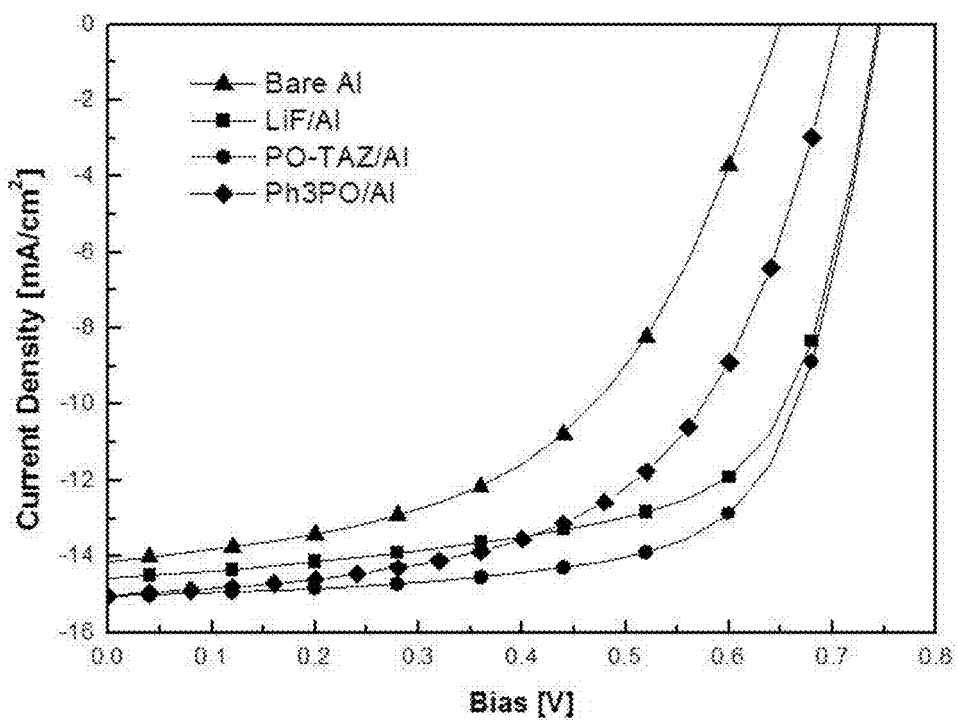
FIG. 6 is a curve showing J-V property of COSC manufactured by Example 18.
Figure 7:
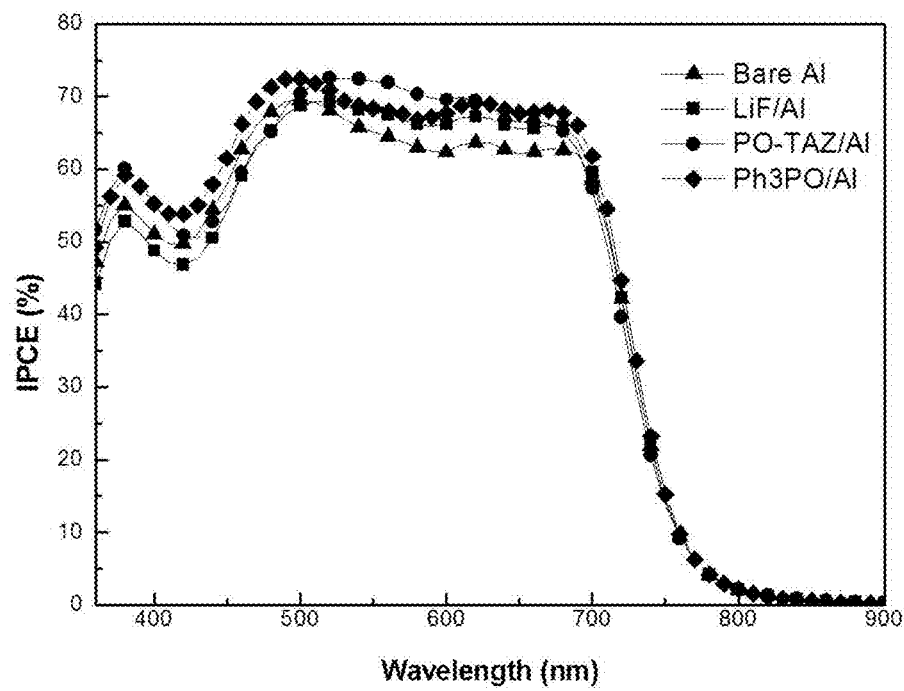
FIG. 7 shows EQE spectra of COSC manufactured by Example 18.

The manufactured device was manufactured in a structure of ITO/PEDOT:PSS (35 nm)/PTB7:PC$_{71}$BM(100 nm)/PO-TAZ(5 nm)/Al(100 nm) [FIG. 4], and had a photoactive area of 0.09 cm$^2$ Meanwhile, FIG. 5 shows a HOMO LUMO energy level diagram of the COSC manufactured as above, wherein the HOMO and LUMO of the PO-TAZ were measured to be −8.44 and −4.45 eV, respectively. From the result, an optical band gap ($E_g^{opt}$) of the PO-TAZ prepared by Example 1 was calculated to be 3.99 eV. In addition, a current density-voltage (J-V) and an external quantum efficiency (EQE) were shown in FIGS. 6 and 7, respectively.

[Example 19] Manufacture of IOSC (Inverted Organic Solar Cell)

A ZnO precursor solution was spin-coated on an ITO glass substrate having a sheet resistance (R$_{sheet}$) of 12 Ω/sq, and thermal-treated at 150° C. for 10 minutes to form a ZnO layer having a thickness of 60 nm. The PO-TAZ (0.05 mg) prepared by Example 1 was dissolved in isopropanol (1 mL), followed by spin-coating on the ZnO layer, to form a PO-TAZ layer having a thickness of 5 nm.

PTB7 and PC$_{71}$BM were used for the photoactive layer. PTB7 (8 mg) and PC$_{71}$BM (12 mg) were dissolved in CB (1 mL) and stirred at 50° C. for 12 hours, and DIO (3 vol %) was added thereto, followed by spin-coating on the PO-TAZ layer, to form a photoactive layer having a thickness of 100 nm.

PEDOT:PSS (Clevios P VP AI 4083, filtered at 0.45 μm) was diluted with isopropanol at a ratio of 1:10, followed by spin-coating on the photoactive layer, to form a PEDOT:PSS layer having a thickness of 10 nm.

Finally, the top-electrode Ag metal having a thickness of 150 nm was deposited through a shadow mask by thermal evaporation in a vacuum of approximately $3 \times 10^{-6}$ Torr.

Figure 8:
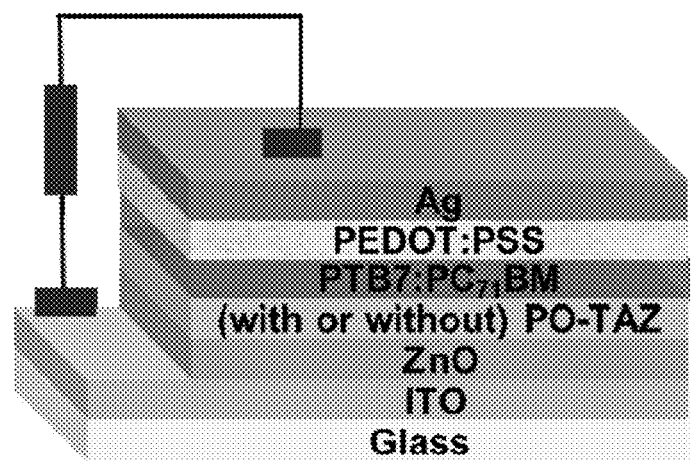
FIG. 8 shows a structure of IOSC manufactured by Example 19.

The manufactured device was manufactured in a structure of ITO/ZnO(60 nm)/PO-TAZ(5 nm)/PTB7:PC$_{71}$BM(100 nm)/PEDOT:PSS(10 nm)/Ag(150 nm) [FIG. 8], and device areas defined through the shadow mask were 0.11 and 0.38 cm$^2$, respectively.

Figure 9:
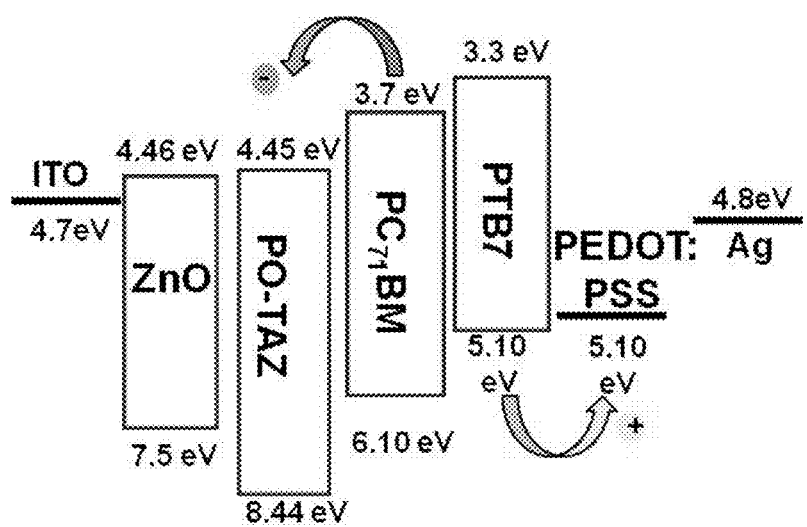
FIG. 9 shows a HOMO LUMO energy level diagram of IOSC manufactured by Example 19.
Figure 10:
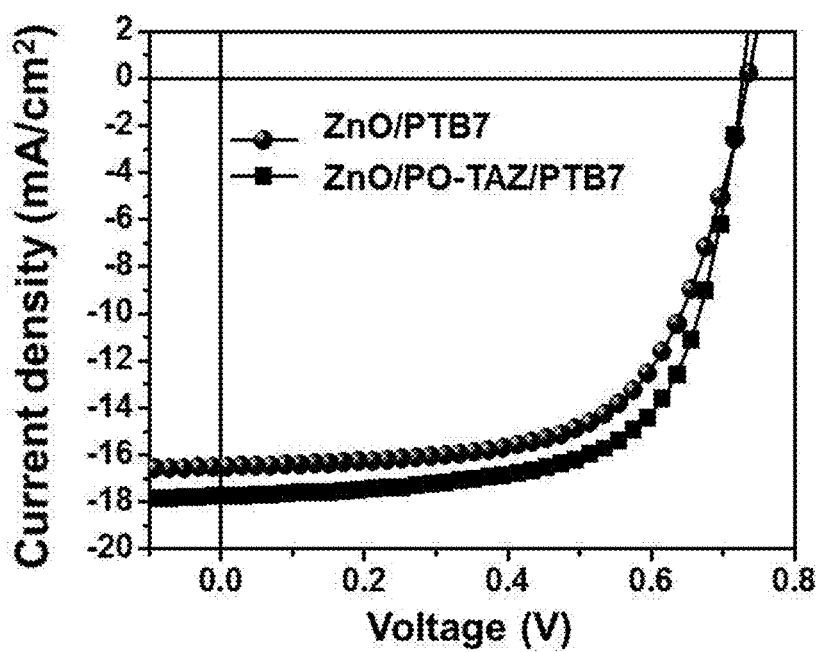
FIG. 10 is a curve showing J-V property of IOSC manufactured by Example 19.
Figure 11:
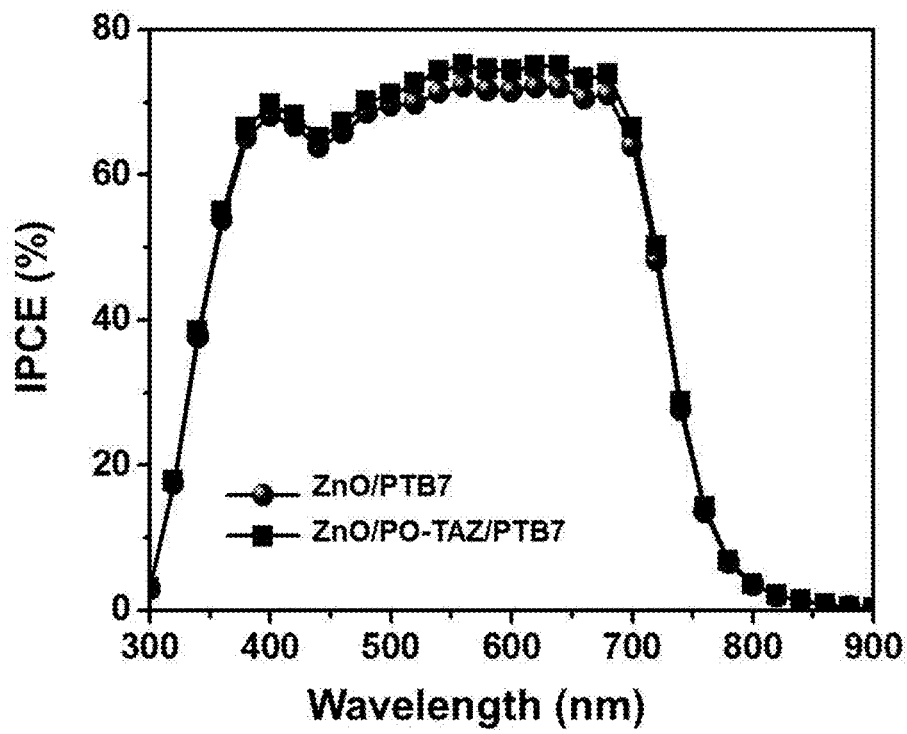
FIG. 11 shows EQE spectra of IOSC manufactured by Example 19.

Meanwhile, FIG. 9 shows a HOMO LUMO energy level diagram of the IOSC manufactured as above, wherein the HOMO and LUMO of the PO-TAZ were measured to be −8.44 and −4.45 eV, respectively. From the result, an optical band gap ($E_g^{opt}$) of the PO-TAZ prepared by Example 1 was calculated to be 3.99 eV. In addition, a current density-voltage (J-V) and external quantum efficiency (EQE) were shown in FIGS. 10 and 11, respectively.

[Example 20] Manufacture of PSC (Perovskite Solar Cell)

A ZnO precursor solution was spin-coated on an ITO substrate, and annealed at 150° C. for 10 minutes to form an ZnO layer having a thickness of 60 nm.

The PO-TAZ (0.05 mg) prepared by Example 1 was dissolved in isopropanol (1 mL), followed by spin-coating on the ZnO layer, to form a PO-TAZ layer having a thickness of 5 nm.

A 0.87M PbI$_2$ DMF solution was spin-coated on the PO-TAZ layer to form a PbI$_2$ layer, and dried in the air, followed by spin-coating with methyl ammonium iodide (MAI) 2-propanol solution (40 mg/mL), to form a MAPbI$_3$ perovskite layer having a thickness of 250 nm.

Spiro-MeOTAD (80 mg) was dissolved in CB (1 mL), and t-BP(t-butyl pyridine) (28.5 μL) and Li-TFSI (lithium bis (trifluoro methanesulfonyl)imide, 520 mg LI-TSFI in 1 ml acetonitrile, Sigma-Aldrich, 99.8%) (17.5 μL) were added thereto to prepare a spiro-MeOTAD solution. The prepared spiro-MeOTAD solution was spin-coated on the perovskite layer to form a hole transport layer having a thickness of 200 nm.

Finally, a 150 nm thick Ag electrode was deposited by thermal evaporation.

Figure 12:
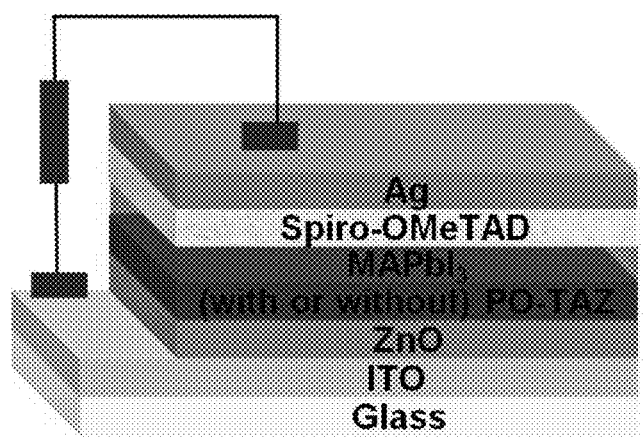
FIG. 12 shows a structure of PSC manufactured by Example 20.

The manufactured device was manufactured in a structure of ITO/ZnO(60 nm)/PO-TAZ(5 nm)/MAPbI$_3$(250 nm)/Spiro-OMeTAD(200 nm)/Ag(150 nm) [FIG. 12].

Figure 13:
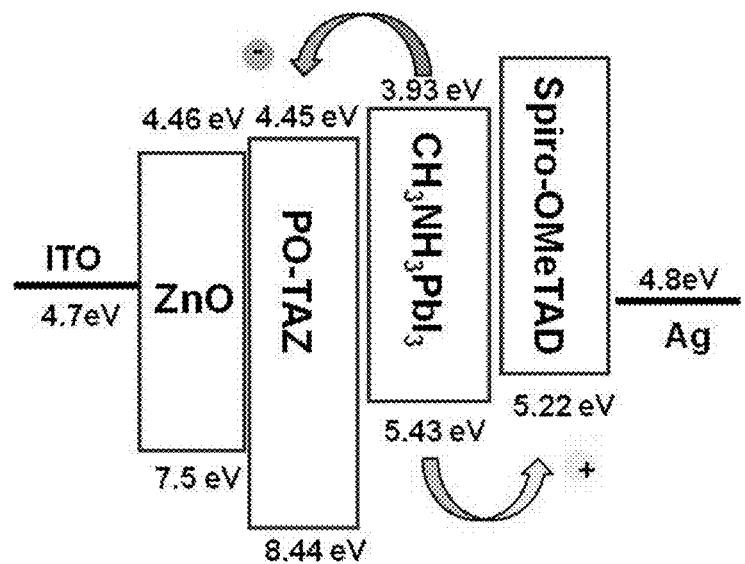
FIG. 13 shows a HOMO LUMO energy level diagram of PSC manufactured by Example 20.
Figure 14:
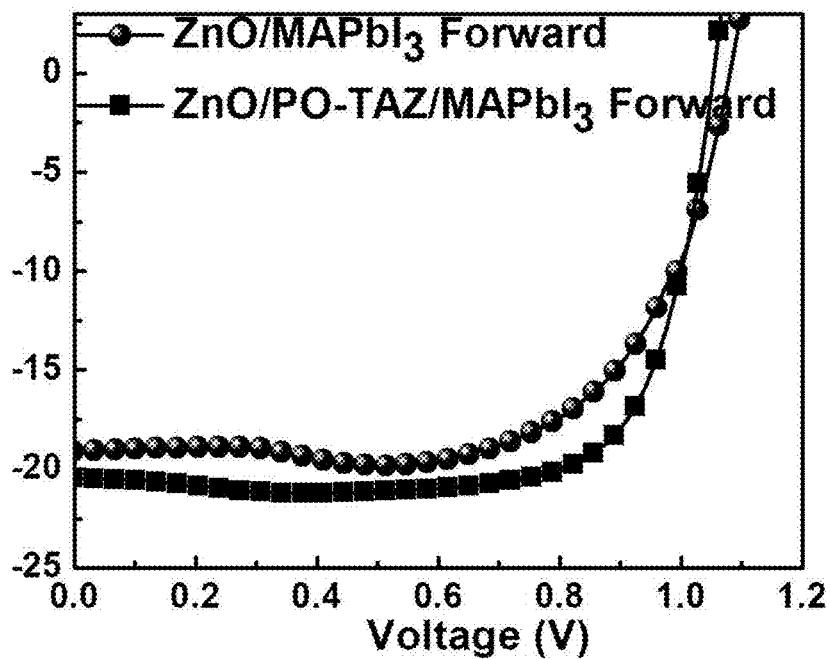
FIG. 14 is a curve showing J-V property of PSC manufactured by Example 20.
Figure 15:
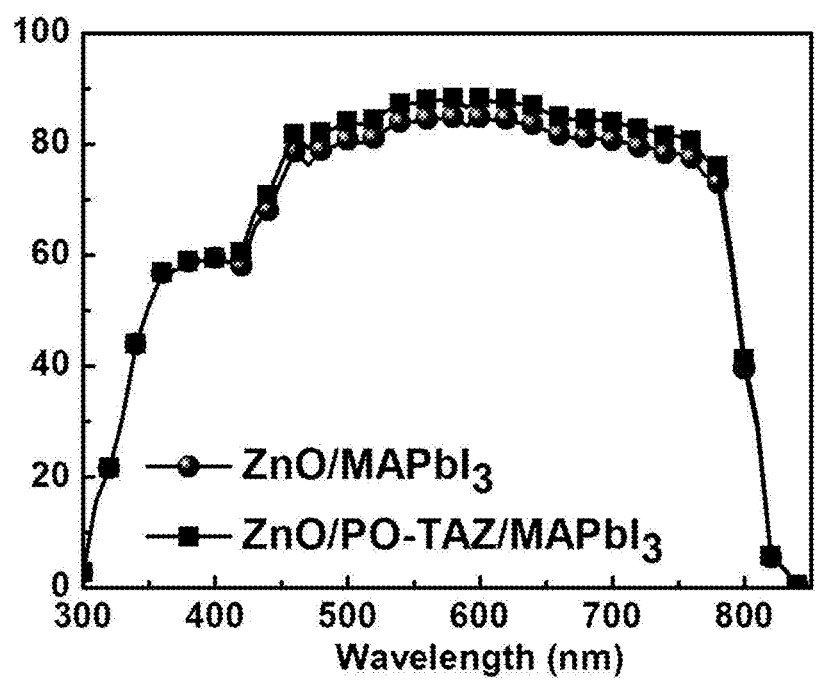
FIG. 15 shows EQE spectra of PSC manufactured by Example 20.

Meanwhile, FIG. 13 shows a HOMO LUMO energy level diagram of the PSC manufactured as above, wherein the HOMO and LUMO of the PO-TAZ were measured to be −8.44 and −4.45 eV, respectively. From the result, an optical bandgap ($E_g^{opt}$) of the PO-TAZ prepared by Example 1 was calculated to be 3.99 eV. In addition, a current density-voltage (J-V) and an external quantum efficiency (EQE) were shown in FIGS. 14 and 15, respectively.

[Example 21] Manufacture of OFET (Organic Field-Effect Transistor)

An organic field-effect transistor (OFET) having a bottom-contact and top-gate structure was manufactured on the pre-treated glass substrate.

Au (20 nm) bottom-contact source/drain electrodes were deposited by thermal evaporation after lithography process.

Poly{[N,N'-bis(2-octyldodecyl)-naphthalene-1,4,5,8-bis (dicarboximide)-2,6-diyl]-alt-5,5'-(2,2'-bithiophene)} (P(NDI2OD-T2), Polyera ActivInk™N2200) which is an n-type semiconductor material was dissolved in chlorobenzene to prepare a solution of which a concentration is 1 wt %, and then, an organic semiconductor layer was formed by a spin coating method.

1 wt % of poly(methyl methacrylate) (PMMA) solution prepared by using 1,2-dichlorobenzene as a solvent was spin-coated on the organic semiconductor layer to form an organic insulation layer, followed by annealing at 80° C. for 20 minutes.

All spin-coating and annealing processes were carried out in a glove box filled with nitrogen.

The aluminum (50 nm) gate electrode was deposited by thermal evaporation through the shadow mask.

The device had a length of 20 μm and a width of 1000 μm. Properties of the OTFT were measured by Keithley 4800.

[Example 22] Manufacture of OTFT (Organic Thin Film Transistor)

OTFT was manufactured in a glove box filled with nitrogen (oxygen content<0.1 ppm, moisture content<0.1 ppm).

For the bottom-gate top source/drain contact $PC_{71}BM$ TFT, an n-doped silicon was used as a gate and $SiO_2$ was used as an insulator.

A $PC_{71}BM$ layer having a thickness of 30 nm was formed and annealed at 1200 for 20 minutes.

The PO-TAZ (0.05 mg) prepared by Example 1 was dissolved in isopropanol (1 mL), followed by spin-coating on the $PC_{71}BM$ layer, to form a PO-TAZ layer having a thickness of 5 nm. The PO-TAZ layer was annealed at 1200 for 20 minutes. Lastly, a 50 nm-thick Au electrode was deposited through a shadow mask.

The device had a length of 20 μm and a width of 1000 μm. Properties of the OTFT were measured by Keithley 4800.

Properties of Compounds

A decomposition temperature ($T_d$) of the PO-TAZ prepared by Example 1 was measured by TGA and the result was shown in FIG. 1, from which it was confirmed that $T_d$ of PO-TAZ was above 300° C. Accordingly, it could be appreciated that the PO-TAZ of the present disclosure is thermally stable.

Figure 2:
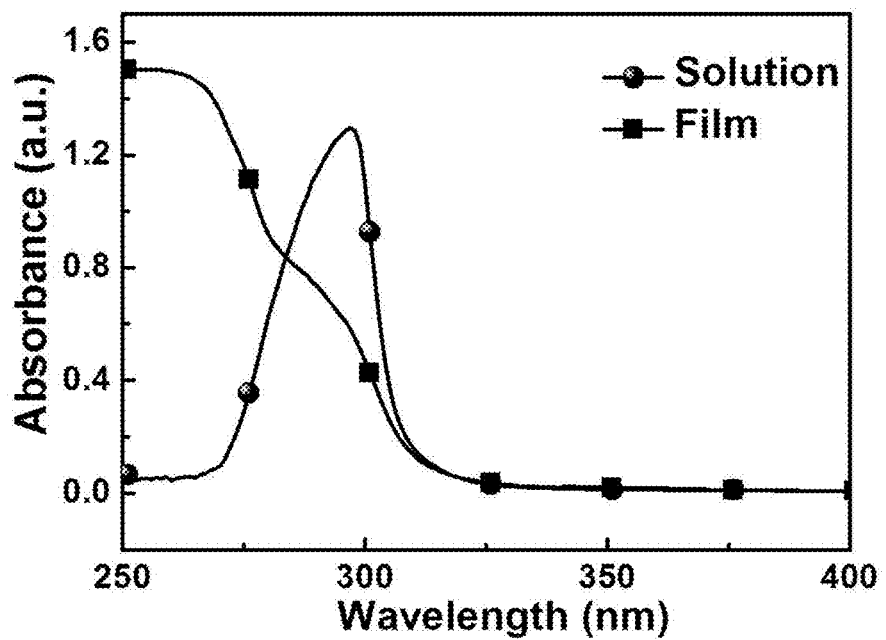
FIG. 2 shows UV-visible absorption spectrum of PO-TAZ prepared by Example 1.

UV-visible absorption spectra of the PO-TAZ prepared by Example 1 were measured in a solution state and in a film state, and the result was shown in FIG. 2, from which it was confirmed that an optical band gap ($E_g^{opt}$) of the PO-TAZ prepared by Example 1 was calculated to be 3.99 eV.

Figure 3:
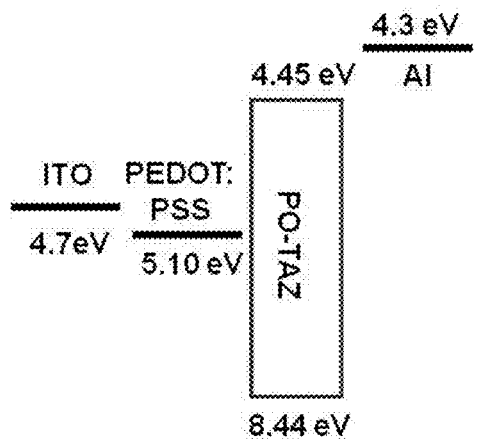
FIG. 3 shows a HOMO LUMO energy level of PO-TAZ prepared by Example 1.

Meanwhile, the HOMO LUMO energy level of the PO-TAZ prepared by Example 1 was measured by UPS (ultraviolet photoelectron spectroscopy) and an optical band gap, and HOMO and LUMO of the PO-TAZ were measured to be −8.44 and −4.45 eV, respectively [FIG. 3]. The measured values were obtained by the triazine unit and the substitution of the electron acceptor P=O in the PO-TAZ, and the PO-TAZ having a low LUMO level as compared to $PC_{71}BM$ (3.7 eV) and Perovskite ($MAPbI_3$) (3.93 eV) could effectively perform electron extraction from the photoactive layer to the electrodes.

Properties of Solar Cell

An AM (air mass) 1.5 G solar simulator (Oriel Sol3A Class AAA solar simulator, models94043A) having a light intensity of 100 mW/cm² was used to investigate photoelectric energy properties of the device.

Electrical properties of the solar cell devices manufactured by Examples 18 to 20, that is, photovoltaic parameters of a maximum power conversion efficiency (PCE), an open circuit voltage ($V_{OC}$), a short-circuit current density ($J_{SC}$) and a fill factor (FF), were shown in Table 1.

TABLE 1

| | Photoactive layer (Device type) | PO-TAZ interlayer | max. PCE [%] | $J_{SC}$ [mA/cm²] | FF [%] | $V_{OC}$ [V] |
|---|---|---|---|---|---|---|
| Ex. 18 | PTB7:$PC_{71}BM$ (Conventional) | ○ | 7.72 | 15.04 | 68.81 | 0.74 |
| Comparative Ex. 1 | PTB7:$PC_{71}BM$ (Conventional) | X | 4.75 | 14.12 | 51.79 | 0.65 |
| Ex. 19 | PTB7:$PC_{71}BM$ (Inverted)[a] | ○ | 9.93 | 18.85 | 68.85 | 0.74 |
| Comparative Ex. 2 | PTB7:$PC_{71}BM$ (Inverted)[a] | X | 8.72 | 18.11 | 65.70 | 0.72 |
| Ex. 20 | Perovskite (Conventional)[b] | ○ | 16.41 | 20.53 | 75.92 | 1.06 |
| | Perovskite (Conventional)[c] | ○ | 16.06 | 20.11 | 75.23 | 1.06 |
| Comparative Ex. 3 | Perovskite (Conventional)[b] | X | 13.92 | 19.19 | 67.26 | 1.06 |
| | Perovskite (Conventional)[c] | X | 13.28 | 18.94 | 65.61 | 1.06 |

[a] Active layer cell area: 0.11 cm²;
[b] Forward direction;
[c] Reverse direction As shown in Table 1 above, the solar cells manufactured by Examples 18 to 20 included the PO-TAZ as the interface material, such that maximum power conversion efficiency (PCE) thereof was more excellent than those of Comparative Examples 1 to 3 that did not include the PO-TAZ.

Properties of Device

Figure 16:
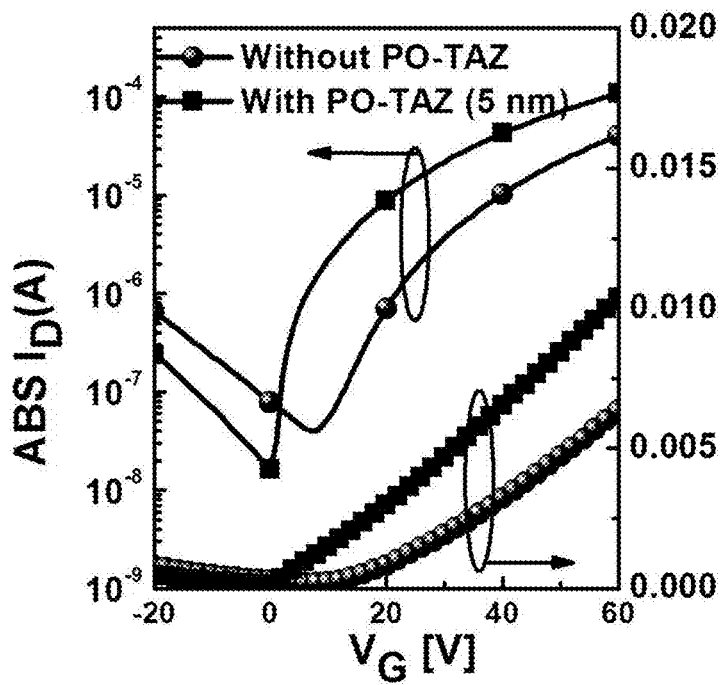
FIG. 16 shows a transfer curve and an out-put curve of a device manufactured by Example 21.
Figure 17:
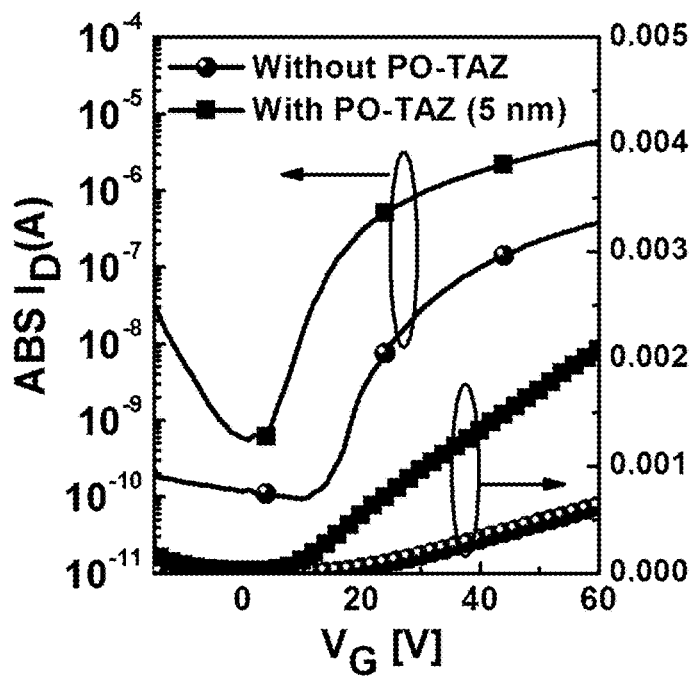
FIG. 17 shows a transfer curve and an out-put curve of a device manufactured by Example 22.

A transfer curve and an out-put curve of the devices manufactured by Examples 21 and 22 were shown in FIGS. 16 and 17, respectively, and properties of the devices manufactured by Examples 21 and 22 were measured at $V_D$(drain voltage)+60V, and the result was shown in Table 2 below.

TABLE 2

| | Device | Electrode | Electron mobility ($\mu_e$) (cm²/vs) | Threshold voltage ($V_{Th}$) [V] | On/Off Ratio ($I_{on/off}$) |
|---|---|---|---|---|---|
| Ex. 21 | P(NDI2OD-T2) (TGBC structure) | POTAZ/Au | 0.52 (±0.04) | 1.4 | $10^4$ |
| Comparative Ex. 4 | P(NDI2OD-T2) (TGBC structure) | Pristine Au | 0.43 (±0.01) | 6.5 | $10^4$ |
| Ex. 22 | $PC_{71}BM$ (TGBC structure) | POTAZ/Au | 0.12 (±0.007) | 12.8 | $10^3$ |
| | $PC_{71}BM$ (BGTC structure) | POTAZ/Au | 0.03 (±0.05) | 4.6 | $10^3$ |
| Comparative Ex. 5 | $PC_{71}BM$ (TGBC structure) | Pristine Au | 0.07 (±0.004) | 4.6 | $10^3$ |
| | $PC_{71}BM$ (BGTC structure) | Pristine Au | 0.004 (±0.1) | 18.7 | $10^3$ |

As shown in Table 2 above, the devices manufactured by Examples 21 and 22 included the PO-TAZ as the electrode interface layers, such that a charge mobility thereof was more excellent and a threshold voltage thereof was lower than those of Comparative Examples 4 and 5 that did not include the PO-TAZ.

The phosphine oxide functionalized triazine derivative according to the present disclosure is prepared by facile protocol with extremely inexpensive 2,4,6-trichloro-1,3,5-triazine (cyanuric chloride) as a starting material, which is economical, and has good solubility in environmentally friendly solvents such as alcohols as well as compatibility with a large area printing process.

The functionalized 1,3,5-triazine moiety having the phosphine oxide group is incorporated into an electron injection interlayer, such that injection and extraction of the electrons with the metal electrode having a high work function (WF) in the electronic devices, particularly, in organic and organic-inorganic (perovskite) solar cells and organic field-effect transistors may be effectively achieved.

In addition, the phosphine oxide functionalized triazine derivative according to the present disclosure is applied as an interface material to exhibit remarkably improved electron injection property, thereby exhibiting significantly excellent maximum power conversion efficiency.

According to the incorporation of the phosphine oxide functionalized triazine derivative of the present disclosure, a low-priced printing process and tremendous improvement in device efficiencies and ambient stability, etc., may be achieved, such that an optoelectronic device is capable of being effectively manufactured in large-areas roll-to-roll process.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and "one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An electronic device comprising:
a phosphine oxide functionalized triazine represented by Chemical Formula 1 below as an interface material:

[Chemical Formula 1]

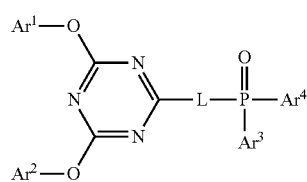

in Chemical Formula 1,
$Ar^1$ and $Ar^2$ are each independently (C6-C20)aryl unsubstituted or substituted with fluorine;
L is (C6-C20)arylene substituted with at least one fluorine;
$Ar^3$ and $Ar^4$ are each independently (C1-C20)alkyl, (C6-C20)aryl, or (C3-C20)heteroaryl, wherein the alkyl, aryl, or heteroaryl of $Ar^3$ and $Ar^4$ may be further substituted with at least one selected from (C1-C20)alkyl, halo(C1-C20)alkyl, (C1-C20)alkoxy, and halo(C1-C20)alkoxy; and
the heteroaryl includes at least one heteroatom selected from N, O, and S,
wherein the electronic device is at least one selected from an organic solar cell, a perovskite solar cell, an organic field-effect transistor, and an organic thin film transistor.

2. The electronic device of claim 1, wherein L is (C6-C20)arylene substituted with at least two fluorines.

3. The electronic device of claim 1, wherein $Ar^1$ and $Ar^2$ are each independently phenyl, biphenyl, naphthyl, anthryl, phenanthryl, tetracenyl, pyrenyl, or perylenyl, the phenyl, biphenyl, naphthyl, anthryl, phenanthryl, tetracenyl, pyrenyl, or perylenyl of $Ar^1$ and $Ar^2$ may be further substituted with at least one fluorine; $Ar^3$ and $Ar^4$ are each independently methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, or pyrazinyl, the methyl, ethyl, propyl, butyl, pentyl, hexyl, heptyl, octyl, phenyl, biphenyl, naphthyl, anthryl, phenanthryl, tetracenyl, pyrenyl, perylenyl, furyl, thienyl, pyridyl, thiazolyl, oxazolyl, quinolyl, indolyl, pyrimidyl, or pyrazinyl of $Ar^3$ and $Ar^4$ may be further substituted with at least one selected from methyl, ethyl, propyl, butyl, trifluoromethyl, perfluoroethyl, methoxy, trifluoromethoxy, and perfluoroethoxy.

4. The electronic device of claim 2, wherein L is phenylene, biphenylene, naphthylene, anthrylene, phenanthrylene, tetracenylene, pyrenylene, or perylenylene substituted with at least two fluorines.

5. The electronic device of claim 4, wherein the phosphine oxide functionalized triazine is represented by Chemical Formulas 2 to 4 below:

[Chemical Formula 2]

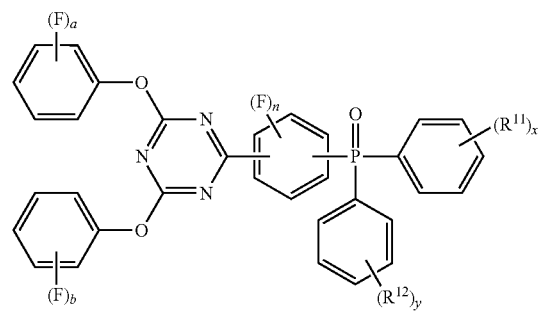

[Chemical Formula 3]

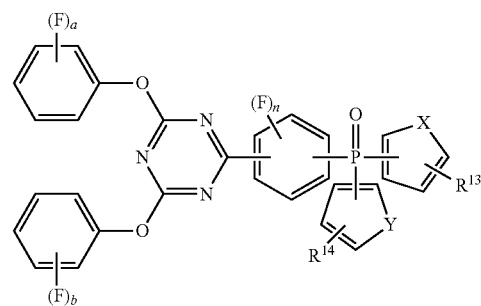

[Chemical Formula 4]

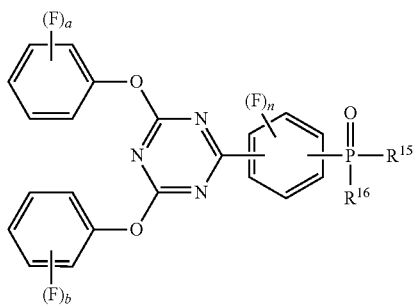

in Chemical Formulas 2 to 4, a and b are each independently an integer from 0 to 5; n is an integer from 2 to 4; $R^{11}$ and $R^{12}$ are each independently (C1-C20)alkyl, halo(C1-C20)alkyl, (C1-C20)alkoxy, or halo(C1-C20)alkoxy; x and y are each independently an integer from 0 to 5; X and Y are each independently NH, O, or S; $R^{13}$ and $R^{14}$ are each independently hydrogen, (C1-C20) alkyl, halo(C1-C20)alkyl, (C1-C20)alkoxy, or halo(C1-C20)alkoxy; $R^{15}$ and $R^{16}$ are each independently (C1-C20)alkyl, the alkyl of $R^{15}$ and $R^{16}$ may be further substituted with at least one selected from (C1-C20) alkyl, halo(C1-C20)alkyl, (C1-C20)alkoxy, and halo(C1-C20)alkoxy.

6. The electronic device of claim 5, wherein the phosphine oxide functionalized triazine is selected from the following compounds:

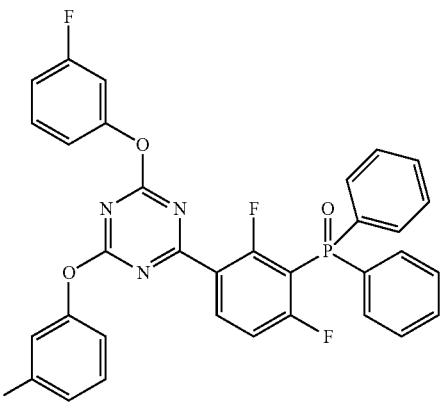

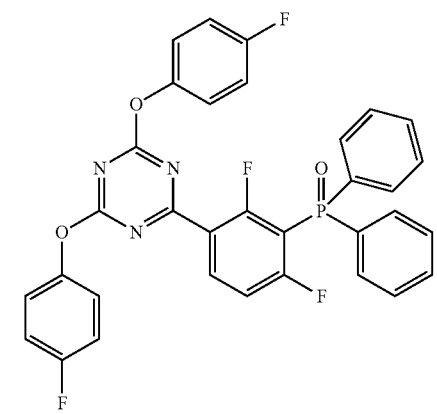

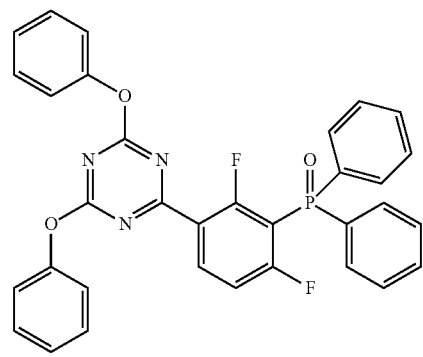

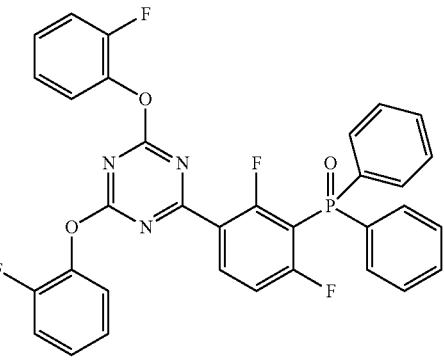

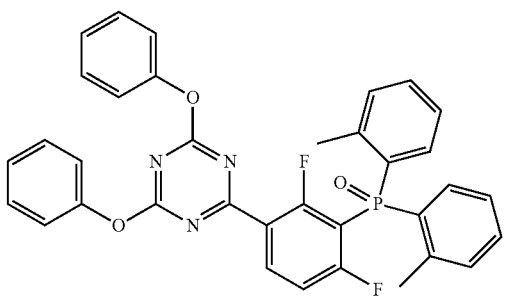

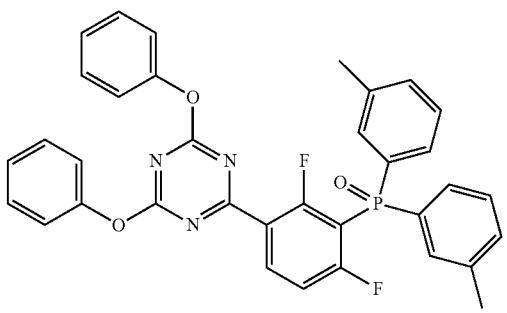

53
-continued
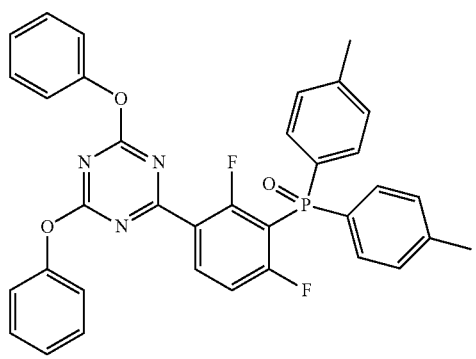
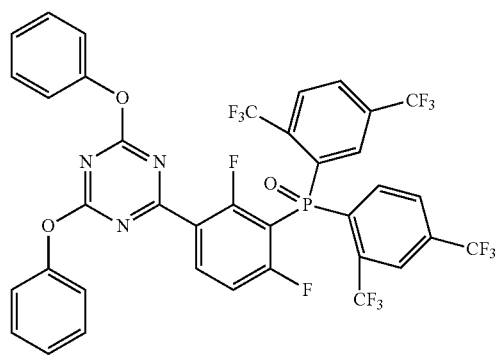
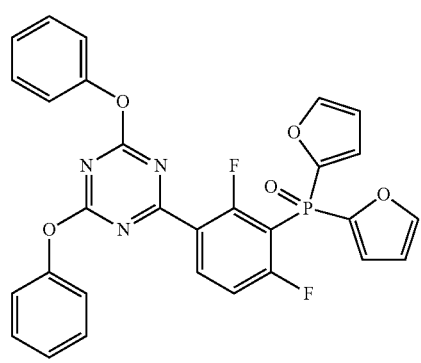
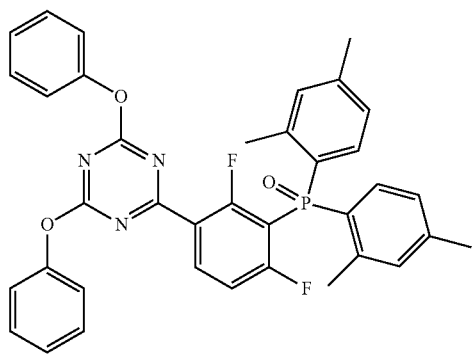
54
-continued
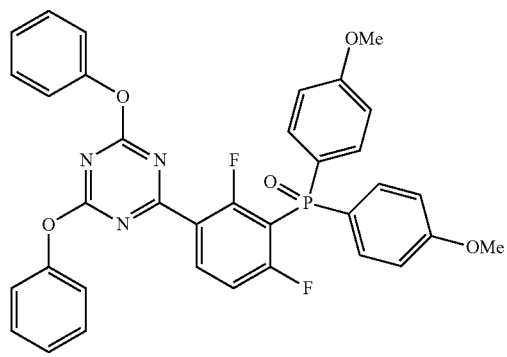
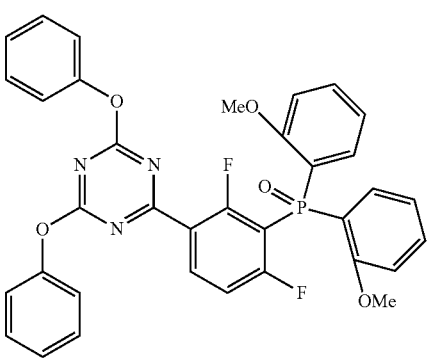
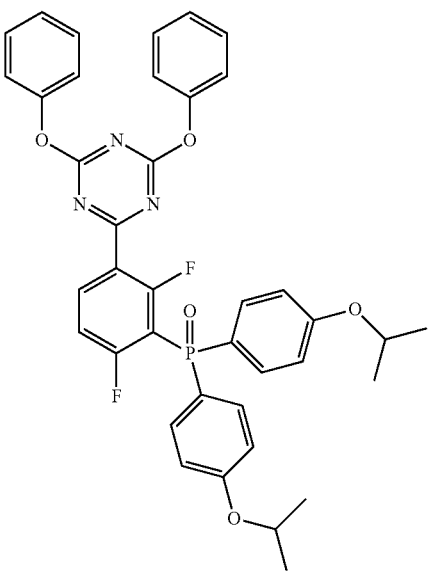

-continued

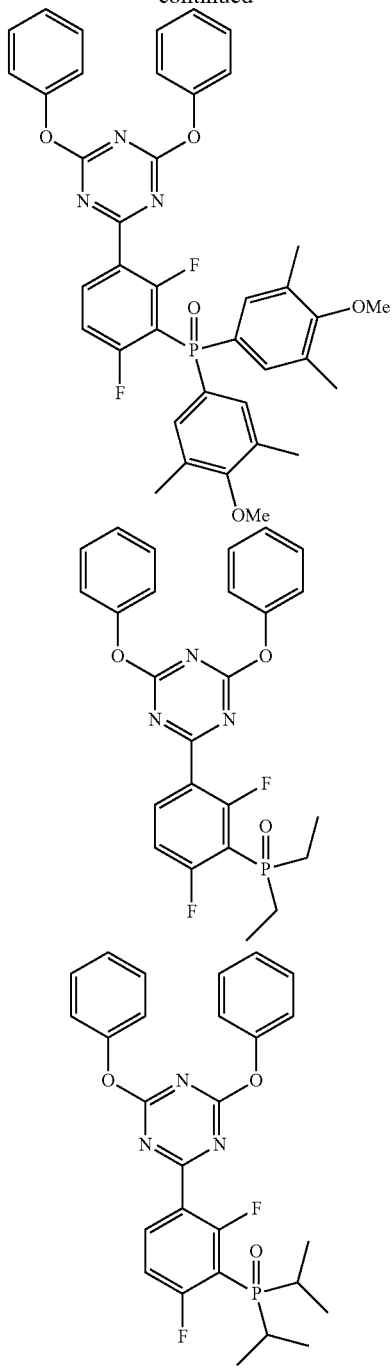

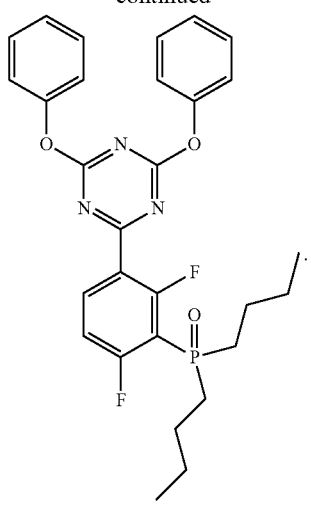

7. A phosphine oxide functionalized triazine represented by Chemical Formula 1 below:

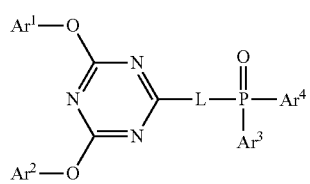

[Chemical Formula 1]

in Chemical Formula 1, $Ar^1$ and $Ar^2$ are each independently (C6-C20)aryl unsubstituted or substituted with fluorine;

L is (C6-C20)arylene substituted with at least one fluorine; and $Ar^3$ and $Ar^4$ are each independently (C1-C20)alkyl, (C6-C20)aryl, or (C3-C20)heteroaryl, wherein the alkyl, aryl or heteroaryl of $Ar^3$ and $Ar^4$ may be further substituted with at least one selected from (C1-C20) alkyl, halo(C1-C20)alkyl, (C1-C20)alkoxy, and halo(C1-C20)alkoxy.

* * * * *